United States Patent
Ando

(10) Patent No.: US 12,342,774 B2
(45) Date of Patent: Jul. 1, 2025

(54) MELON VARIETY NUN 71560 MEM

(71) Applicant: NUNHEMS B.V., Nunhem (NL)

(72) Inventor: Kaori Ando, Acampo, CA (US)

(73) Assignee: NUNHEMS B.V., Nunhem (NL)

( * ) Notice: Subject to any disclaimer, the term of this patent is extended or adjusted under 35 U.S.C. 154(b) by 301 days.

(21) Appl. No.: 18/071,186

(22) Filed: Nov. 29, 2022

(65) Prior Publication Data

US 2023/0148501 A1    May 18, 2023

(51) Int. Cl.
*A01H 6/34* (2018.01)
*A01H 5/08* (2018.01)

(52) U.S. Cl.
CPC .............. *A01H 6/344* (2018.05); *A01H 5/08* (2013.01)

(58) Field of Classification Search
CPC ..................................................... A01H 6/344
See application file for complete search history.

(56) References Cited

U.S. PATENT DOCUMENTS

| | | | |
|---|---|---|---|
| 10,334,797 | B2 | 7/2019 | Ogundiwin et al. |
| 2015/0126380 | A1 | 5/2015 | Van Dun |
| 2015/0245570 | A1 | 9/2015 | Vogelaar et al. |
| 2017/0071145 | A1 | 3/2017 | Tadmor et al. |
| 2017/0240913 | A1 | 8/2017 | Schaffer et al. |
| 2017/0335339 | A1 | 11/2017 | Van Dun et al. |

OTHER PUBLICATIONS

"*Cucumis melo* L.: Melon", Calibration Book, Natktuinbouw, Version 1, Dec. 2010, 114 pages.
"Melon-UPOV Code: CUCUM_MEL(*Cucumis melo* L.) ", Guidelines for the Conduct of Tests for Distinctness, Uniformity and Stability, UPOV, International Union for the Protection of New Varieties of Plants, Geneva, TG/104/5, Revision 2, Oct. 29, 2019, 69 pages.
"Objective description of variety: Muskmelon/Cantaloupe (*Cucumis melo* L.)", US Department of Agriculture, Agricultural Marketing Service, Science and Technology, Plant Variety Protection Office, Exhibit C, Jun. 2015, 04 pages.
Colijn-Hooymans, et al., "Competence for regeneration of cucumber cotyledons is restricted to specific developmental stages", Plant Cell, Tissue and Organ Culture, vol. 39, Dec. 1994, pp. 211-217.
Hartz, et al., "Cantaloupe Production in California", University of California Division of Agriculture and Natural Resources, Publication 7218, 1996, pp. 1-4.
Mayberry, et al., "Mixed melon production in California", University of California Agriculture and Natural Resources, Publication 7209, 1996, pp. 1-3.
Needleman, et al., "A general method applicable to the search for similarities in the amino acid sequence of two proteins", Journal of Molecular Biology, vol. 48, Issue 3, 1970, pp. 443-453.
Nikolova, et al., "Diploidization of cucumber (*Cucumis sativus* L.) haploids by colchicine treatment", Acta Societas Botanicorum Poloniae, vol. 65, Issue 3-4, 1996, pp. 311-317.
Parvathaneni, et al., "Fingerprinting in Cucumber and Melon (*Cucumis* spp.) Genotypes Using Morphological and ISSR Markers", Journal of Crop Science and Biotechnology, vol. 14, Issue 1, Mar. 2011, pp. 39-43.
Ren, et al., "Shoot regeneration and ploidy variation in tissue culture of honeydew melon (*Cucumis melo* L. inodorus)", In Vitro Cellular & Developmental Biology—Plant, vol. 49, Dec. 21, 2012, pp. 223-229.
Rice, et al., "EMBOSS: The European Molecular Biology Open Software Suite", Trends in Genetics, vol. 16, Issue 6, Jun. 1, 2000, pp. 276-277.
Songstad, et al., "Genome Editing of Plants", Critical Reviews in Plant Sciences, vol. 36, Issue 1, 2017, pp. 1-23.
Vidavsky, et al., "Tomato Breeding Lines Resistant and Tolerant to Tomato Yellow Leaf Curl Virus Issued from *Lycopersicon hirsutum*", The American Phytopathology Society, vol. 88, Issue 9, Sep. 1998, pp. 910-914.
Vos, et al., "AFLP: a new technique for DNA fingerprinting", Nucleic Acids Research, vol. 23, Issue 21, Nov. 11, 1995, pp. 4407-4414.
Wijnker, et al., "Hybrid recreation by reverse breeding in *Arabidopsis thaliana*", Nature Protocols, vol. 9, Issue 4, Mar. 6, 2014, pp. 761-772.

*Primary Examiner* — Brent T Page
(74) *Attorney, Agent, or Firm* — ArentFox Schiff LLP

(57) ABSTRACT

A new and distinct melon variety NUN 71560 MEM is disclosed as well as seeds and plants and fruits thereof. NUN 71560 MEM is a Honey Dew melon variety, comprising resistance to *Fusarium oxysporum* f. sp. *melonis* Race 0 and Race 2, *Podosphaera xanthii* Race 5, and *Aphis gossypii*.

29 Claims, 4 Drawing Sheets

MELON VARIETY NUN 71560 MEM

FIELD OF THE DISCLOSURE

The disclosure relates to the field of plant breeding and, more specifically, to melon variety NUN 71560 MEM. The disclosure further relates to vegetative reproductions of melon variety NUN 71560 MEM, methods for tissue culture of melon variety NUN 71560 MEM, and regenerating a plant from such a tissue culture and to phenotypic variants of melon variety NUN 71560 MEM. The disclosure also relates to progeny of melon variety NUN 71560 MEM and the hybrid varieties obtained by crossing melon variety NUN 71560 MEM as a parent line with plants of other varieties or parent lines.

BACKGROUND OF THE DISCLOSURE

The goal of plant breeding is to combine various desirable traits in a single variety. Such desirable traits may include greater yield, resistance to diseases, insects or other pests, tolerance to heat and drought, better agronomic quality, higher nutritional value, enhanced growth rate, and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

One crop species which has been subject to such breeding programs and is of particular value is the melon. It belongs to the *Cucurbitacea* family and has originated in Asia. The plant is a large and sprawling annual, grown for its fruit. The fruit of most species of *Cucumis melo* is often colored attractively, commonly yellow, orange or red. Melon can contain black seeds, which are considered undesirable for some uses. Common types include Persian, Honey Dew, Casaba, Crenshaw, Common/Summer and subtypes such as the popular Galia, Canary, Western Shipper or the new Crispy types. Melon is typically consumed fresh as desserts, snacks, or in salads.

One of the leading consumers of melon is the United States with California as the major producer. Melon is available year-round but supply peaks in August and ends in November.

While breeding efforts to date have provided a number of useful melon varieties with beneficial traits, there remains a great need in the art for new varieties with further improved traits. Such plants would benefit farmers and consumers alike by improving crop yields and/or quality. Breeding objectives include varying the color, size, texture and flavor of the fruit, absence of seeds, optimizing flesh thickness, disease or pest resistance, yield, suitability to various climatic circumstances, solid content (% dry matter), sugar content, and storage properties.

SUMMARY OF THE VARIOUS ASPECTS OF THE DISCLOSURE

The disclosure provides for melon variety NUN 71560 MEM, products thereof, and methods of using the same. NUN 71560 MEM is a Honey Dew melon variety and is suitable for growing in the open field.

In another aspect, the plant of melon variety NUN 71560 MEM, or part thereof, or progeny thereof comprises resistance to *Fusarium oxysporum* f. sp. *melonis* Race 2, *Podosphaera xanthii* Race 5, and *Aphis gossypii*, measured according to TG104/5.

In another aspect, the plant of variety NUN 71560 MEM or a progeny thereof has 27, 28, 28, 29, or more or all of the distinguishing characteristics as shown in Table 3 when compared to the Reference Variety when determined at 5% significance level for numerical characteristics and determined by type or degree for non-numerical characteristics for plants grown under the same environmental conditions.
 1. Early maturity cycle;
 2. dark green (RHS N137B) mature leaf color;
 3. longer mature leaf length;
 4. larger mature leaf width;
 5. longer mature leaf petiole length;
 6. dark intensity of green color of mature leaf;
 7. weak leaf blistering;
 8. absent or very sparse density of dots of young fruit;
 9. small size of dots of young fruit;
 10. weak contrast of dot color/ground color of young fruit;
 11. medium length of peduncle of young fruit;
 12. round shape of fruit at edible maturity;
 13. broad diameter of fruit at edible maturity;
 14. small to medium ratio of length/diameter of fruit at edible maturity;
 15. circular shape in longitudinal section of fruit at edible maturity;
 16. medium to large pistil scar of fruit at edible maturity;
 17. white rind color (RHS 155A) at edible maturity;
 18. yellow green flesh color (RHS 145D) near cavity at edible maturity;
 19. yellow green flesh color (RHS 145D) in center at edible maturity;
 20. yellow green flesh color (RHS 145D) near rind at edible maturity;
 21. higher % soluble solids at edible maturity;
 22. less firm flesh (penetrometer reading);
 23. larger seed cavity width;
 24. medium intensity of cream yellow seed color;
 25. no resistance to *Podosphaera xanthii* Race 1;
 26. no resistance to *Podosphaera xanthii* Race 2;
 27. resistant to *Podosphaera xanthii* Race 5; and
 28. resistant to *Aphis gossypii*; and
 29. resistant to *Fusarium oxysporum* f. sp. *melonis* Race 0.

The disclosure also provides for a progeny of melon variety NUN 71560 MEM. In one aspect, the disclosure provides a plant or a progeny retaining all or all but one, two, or three of the "distinguishing characteristics" or all or all but one, two, or three of the "morphological and physiological characteristics" of the plant of melon variety NUN 71560 MEM, and methods for producing that plant or progeny.

In another aspect, the disclosure provides a plant or a progeny having all the physiological and morphological characteristics of the plant of variety NUN 71560 MEM when grown under the same environmental conditions. In another aspect, the plant or progeny has all or all but one, two, or three of the physiological and morphological characteristics of the plant of melon variety NUN 71560 MEM, when measured under the same environmental conditions and e.g., evaluated at significance levels of 1%, 5% or 10% significance (which can also be expressed as a p-value) for quantitative characteristics and determined by type or degree for non-quantitative characteristics, wherein a representative sample of seed of melon variety NUN 71560 MEM has been deposited under Accession Number NCIMB 44082. In another aspect, the plant or progeny has all or all but one, two, or three of the physiological and morphological characteristics as listed in Tables 1 and 2 for melon variety NUN 71560 MEM, when measured under the same environmental conditions and e.g., evaluated at significance levels of 1%, 5% or 10% (which can also be expressed as a p-value) for quantitative characteristics and determined by type or degree for non-quantitative characteristics.

In another aspect, the disclosure provides a seed of melon variety NUN 71560 MEM, wherein a representative sample of said seed has been deposited under Accession Number NCIMB 44082. The disclosure also provides for a plurality of seeds of melon variety NUN 71560 MEM. The melon seed of variety NUN 71560 MEM may be provided as an essentially homogeneous population of melon seed. The population of seed of melon variety NUN 71560 MEM may be particularly defined as essentially free from other seed. The seed population may be grown into plants to provide an essentially homogeneous population of melon plants as described herein.

The disclosure also provides a plant grown from a seed of melon variety NUN 71560 MEM and plant part thereof.

The disclosure further provides a melon fruit produced on a plant grown from a seed of melon variety NUN 71560 MEM.

The disclosure furthermore provides a seed growing or grown on a plant of variety NUN 71560 MEM (i.e., produced after pollination of the flower of melon variety NUN 71560 MEM).

The disclosure also provides a melon plant or part thereof having all of the physiological and morphological characteristics of the plant of melon variety NUN 71560 MEM when grown under the same environmental conditions.

In another aspect, the disclosure provides for a plant part obtained from melon variety NUN 71560 MEM, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, cotyledon, a scion, a stock, a rootstock, a pistil, an anther, or a flower or a part thereof. Fruits are particularly important plant parts. Such plant parts may be suitable for sexual reproduction, vegetative reproduction, or a tissue culture. In another aspect, the plant part obtained from melon variety NUN 71560 MEM is a cell, optionally a cell in a cell or tissue culture. That cell may be grown into a plant of variety NUN 71560 MEM.

In another aspect, the disclosure provides for a hybrid melon variety NUN 71560 MEM.

In another aspect, the disclosure provides a cell culture of melon variety NUN 71560 MEM and a plant regenerated from melon variety NUN 71560 MEM, wherein said plant has all the characteristics of the plant of melon variety NUN 71560 MEM when grown under the same environmental conditions, as well as methods for culturing and regenerating melon variety NUN 71560 MEM. Alternatively, a regenerated plant may have one characteristic that is different from melon variety NUN 71560 MEM and which otherwise has all of the physiological and morphological characteristics of the plant of melon variety NUN 71560 MEM.

The disclosure also provides a vegetatively propagated plant of variety NUN 71560 MEM having all or all but one, two, or three of the morphological and physiological characteristics of melon variety NUN 71560 MEM when grown under the same environmental conditions as well as methods for vegetatively propagating melon variety NUN 71560 MEM.

In another aspect, the disclosure provides a method of producing a melon plant comprising crossing melon variety NUN 71560 MEM with itself or with another melon variety and selecting a progeny melon plant from said crossing.

The disclosure also provides a method of producing a melon plant derived from melon variety NUN 71560 MEM.

In further aspect, the disclosure provides a method of producing a hybrid melon seed comprising crossing a first parent melon plant with a second parent melon plant and harvesting the resultant hybrid melon seed, wherein said first parent melon plant or second parent melon plant is melon variety NUN 71560 MEM. Also provided is a hybrid melon seed produced from crossing a first parent melon plant and second parent melon plant and harvesting the resultant hybrid melon seed, wherein said first parent melon plant or second parent melon plant is melon variety NUN 71560 MEM. Moreover, the hybrid melon plant grown from the hybrid melon seed is provided.

In another aspect, the disclosure provides a method of introducing a single locus conversion into the plant of variety NUN 71560 MEM, wherein a representative sample of seed of said melon variety has been deposited under Accession Number NCIMB 44082, wherein the single locus converted plant comprises the single locus conversion and otherwise has all of the physiological and morphological characteristics of the plant of melon variety NUN 71560 MEM.

In yet another aspect, the disclosure provides a method for introducing a desired trait into melon variety NUN 71560 MEM, said method comprises transforming the plant of variety NUN 71560 MEM with a transgene that confers the desired trait, wherein the transformed plant contains the desired trait and otherwise has all of the physiological and morphological characteristics of the plant of melon variety NUN 71560 MEM.

The disclosure also provides a method of producing a modified melon plant with a desired trait, wherein the method comprises mutating a melon plant or plant part of melon variety NUN 71560 MEM, wherein a representative sample of seed of said melon variety has been deposited under Accession Number NCIMB 44082, and wherein the mutated plant contains the desired trait and otherwise retains all of the physiological and morphological characteristics of melon variety NUN 71560 MEM.

In another aspect, the disclosure provides a method of producing a modified melon, wherein said method comprises mutating a target gene by targeted gene editing in melon plant or plant part of melon variety NUN 71560 MEM, wherein the target gene modified a desired trait.

In one aspect, the single locus conversion or desired trait is male sterility, herbicide tolerance, insect resistance, pest resistance, disease resistance, environmental stress tolerance, modified carbohydrate metabolism, modified protein metabolism, or ripening.

In another aspect, the disclosure provides a container comprising the plant, plant part, or seed of melon variety NUN 71560 MEM.

Also provided is a food, a feed, or a processed product comprising a plant part of melon variety NUN 71560 MEM, wherein the plant part is a fruit or part thereof.

DEFINITIONS

Figure 1:
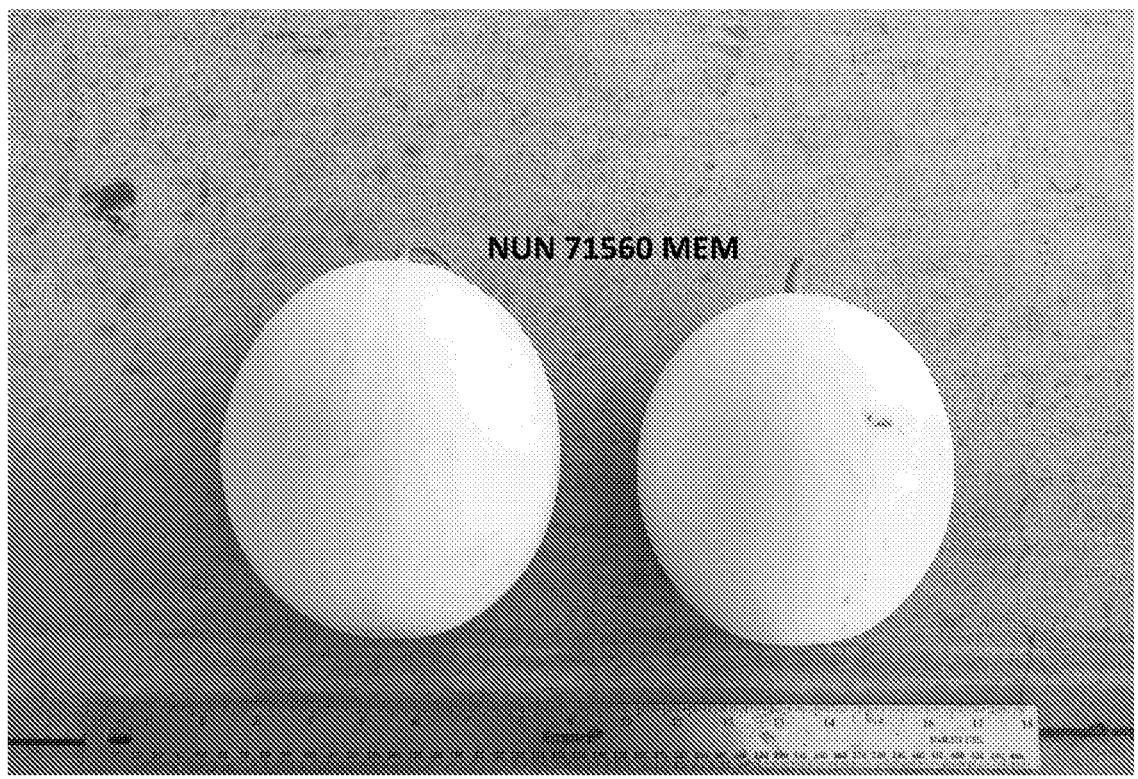
FIG. 1 shows the fruit at edible maturity of melon variety NUN 71560 MEM.
Figure 2:
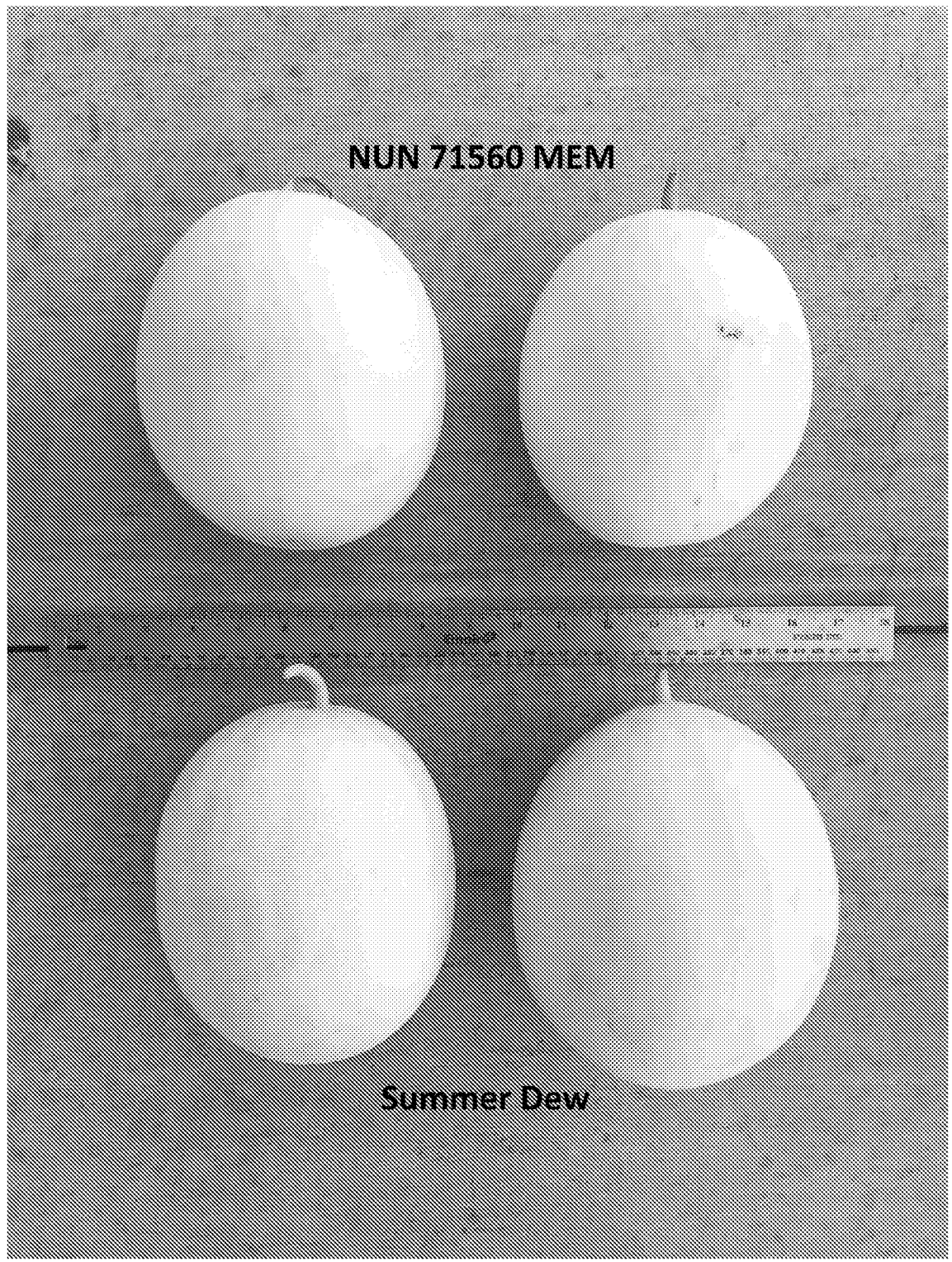
FIG. 2 shows the fruit comparison at edible maturity of melon variety NUN 71560 MEM and the Reference Variety.
Figure 3:
FIG. 3 shows the cross-section comparison at edible maturity of melon variety NUN 71560 MEM and the Reference Variety.
Figure 4:
FIG. 4 shows the mature leaf comparison of melon variety NUN 71560 MEM and the Reference Variety.

"Melon" or "muskmelon" refers herein to plants of the species Cucumis melo, and fruits thereof. The most commonly eaten part of a melon is the fruit or berry, also known as pepo. The fruit comprises exocarp, mesocarp, endocarp or seed cavity, hypanthium tissue and optionally seed. Exocarp, mesocarp, endocarp or seed cavity, hypanthium tissue, and seed coat of the seed are maternal tissues, so they are genetically identical to the plant on which they grow.

"Cultivated melon" refers to plants of Cucumis melo (e.g., varieties, breeding lines or cultivars of the species C. melo), cultivated by humans and having good agronomic characteristics.

"Honey Dew melon" refers to a melon having a slightly oval shape, smooth greenish to yellow skin, and has pale green flesh.

The terms "melon plant designated NUN 71560 MEM," "NUN 71560 MEM," "NUN 71560," "NUN 71560 F1," "71560 MEM," "melon 71560," or "Snow560" are used interchangeably herein and refer to a melon plant of variety NUN 71560 MEM, representative seed of which has been deposited under Accession Number NCIMB 44082.

A "seed of NUN 71560 MEM" refers to a melon seed which can be grown into a plant of variety NUN 71560 MEM, wherein a representative sample of viable seed has been deposited under Accession Number NCIMB 44082. A seed can be in any stage of maturity, for example, a mature, viable seed, or an immature, non-viable seed. A seed comprises an embryo and maternal tissues.

An "embryo of NUN 71560 MEM" refers to a "F1 hybrid embryo" as present in a seed of melon variety NUN 71560 MEM, a representative sample of said seed has been deposited under Accession Number NCIMB 44082.

A "seed grown on NUN 71560 MEM" refers to a seed grown on a mature plant of variety NUN 71560 MEM or inside a fruit of melon variety NUN 71560 MEM. The "seed grown on NUN 71560 MEM" contains tissues and DNA of the maternal parent, melon variety NUN 71560 MEM. The "seed grown on NUN 71560 MEM" contains an F1 embryo.

A "fruit of NUN 71560 MEM" refers to a fruit containing maternal tissues of melon variety NUN 71560 MEM, as deposited under Accession Number NCIMB 44082. In one aspect, the fruit contains seed grown on melon variety NUN 71560 MEM. In another aspect, the fruit does not contain seed, so the fruit is parthenocarpic. The skilled person is familiar with methods for inducing parthenocarpy. Those methods comprise chemically or genetically inducing parthenocarpy. Compounds suitable for chemically inducing parthenocarpy comprise auxins, gibberellins and cytokinins. Methods for genetically inducing parthenocarpy comprise the methods described in US 2017/0335339, US 2017/0240913, and US 2017/0071145. A fruit can be in any stage of maturity, for example, a mature fruit in the yellow stage comprising viable seed, or an immature fruit in the edible green stage comprising non-viable seed.

An "essentially homogeneous population of melon seed" is a population of seeds where at least 97%, 98%, 99% or more of the total population of seed are seeds of melon variety NUN 71560 MEM.

An "essentially homogeneous population of melon plants" is a population of plants where at least 97%, 98%, 99% or more of the total population of plants are plants of melon variety NUN 71560 MEM.

The phrase "essentially free from other seed" refers to a population of seed where less than 3%, 2%, 1% or less of the total population of seed is seed that is not a melon seed or, in another aspect, less than 3%, 2%, 1% or less of the total population of seed is seed that is not seed of melon variety NUN 71560 MEM.

"USDA descriptors" are the plant variety descriptors described for melon in the "Objective description of Variety-Muskmelon/Cantaloupe (Cucumis melo L.)," as published by the US Department of Agriculture, Agricultural Marketing Service, Plant Variety Protection Office (June 2015) and which can be downloaded from the world-wide web at ams.usda.gov/under services/plant-variety-protection/pvpo-c-forms under muskmelon. "Non-USDA descriptors" are other descriptors suitable for describing melon.

"UPOV descriptors" are the plant variety descriptors described for melon in the "Guidelines for the Conduct of Tests for Distinctness, Uniformity and Stability, TG/104/5 (Geneva 2006, as last updated in 2019 Oct. 29), as published by UPOV (International Union for the Protection of New Varieties and Plants) and which can be downloaded from the world-wide web at upov.int/edocs/tgdocs/en/tg104.pdf and is herein incorporated by reference in its entirety. Likewise, "UPOV methods" to determine specific parameters for the characterization of melon are described at upov.int.

"Calibration book Cucumis melo L." refers to the calibration book for melon which provides guidance for describing a melon variety, as published by Naktuinbow (December 2020, version 1) and based on the UPOV Guideline TG/104/5 and CPVO (Community Plant Variety Office) Protocol CPVO-TP/104/2.

"RHS" or "RHS color chart" refers to the color chart of the Royal Horticultural Society (UK), which publishes a botanical color chart quantitatively identifying colors by a defined numbering system. The chart may be purchased from Royal Horticulture Society Enterprise Ltd. RHS Garden; Wisley, Woking; Surrey GU236QB, UK, e.g., the RHS color chart 2007.

"Reference Variety for NUN 71560 MEM" refers herein to variety Summer Dew, a commercial variety from Harris Moran, which have been planted in a trial together with melon variety NUN 71560 MEM. The characteristics of melon variety NUN 71560 MEM were compared to the characteristics of the Reference Variety as shown in Tables 1 and 2. The distinguishing characteristics between melon variety NUN 71560 MEM and the Reference Variety are shown in Table 3.

"Plant" includes the whole plant or any part or derivatives thereof, preferably having the same genetic makeup as the plant from which it is obtained.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, a hypocotyl, a cotyledon, a scion, a graft, a stock, a rootstock, a pistil, an anther, or a flower or part thereof. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises maternal tissues of melon variety NUN 71560 MEM and an embryo having one or two sets of chromosomes derived from the parent plant, e.g., from melon variety NUN 71560 MEM. Such an embryo comprises two sets of chromosomes derived from melon variety NUN 71560 MEM, if it is produced from self-pollination of said variety, while an embryo derived from cross-fertilization of melon variety NUN 71560 MEM will comprise only one set of chromosomes from said variety.

"Rootstock" or "stock" refers to the plant selected for its root system, in particular for the resistance of the roots to diseases or stress (e.g., heat, cold, salinity etc.). Generally, the quality of the fruit of the plant providing the rootstock is less important.

"Scion" refers to a part of the plant attached to the rootstock. This plant is selected for its stems, leaves, flowers, or fruits. The scion contains the desired genes to be duplicated in future production by the stock/scion plant and may produce the desired melon fruit.

"Stock/scion" or "grafted plant" refers to a melon plant comprising a rootstock from one plant grafted to a scion from another plant.

"Grafting" refers to attaching tissue from one plant to another plant so that the vascular tissues of the two tissues join together. Grafting may be done using methods known in the art like: 1) Tongue Approach/Approach Graft; 2) Hole Insertion/Terminal/Top Insertion Graft; 3) One Cotyledon/Slant/Splice/Tube Graft; and 4) Cleft/Side Insertion Graft.

"Flavor" refers to the sensory impression of a food or other substance, especially a melon fruit or fruit part (fruit flesh) and is determined mainly by the chemical senses of taste and smell. Flavor is influenced by texture properties and by volatile and/or non-volatile chemical components (organic acids, lipids, carbohydrates, salts etc.).

"Aroma" refers to smell (or odor) characteristics of melon fruits or fruit parts (fruit flesh).

"Harvest maturity" is referred to as the stage at which a melon fruit is ripe or ready for harvest or the optimal time to harvest the fruit for the market, for processing or for consumption. In one aspect, harvest maturity is the stage which allows proper completion of the normal ripening.

"Harvested plant material" refers herein to plant parts (e.g., fruits detached from the whole plant), which have been collected for further storage and/or further use.

"Yield" means the total weight of all melon fruits harvested per hectare of a particular line or variety. It is understood that "yield" expressed as weight of all melon fruits harvested per hectare can be obtained by multiplying the number of plants per hectare times the "yield per plant."

"Marketable yield" means the total weight of all marketable melon fruits, especially fruit which is not cracked, damaged or diseased, harvested per hectare of a particular line or variety. A "marketable fruit" is a fruit that has commercial value.

"Refractometer % of soluble solids" refers to the percentage of soluble solids in fruit juice. It is also expressed as ° Brix and indicates sweetness. The majority of soluble solids in melon are mainly sugars present in the fruits of melon hence, the correlation with sweetness. Brix can be measured using a Brix meter (also known as Refractometer).

"Netted" skin or rind refers to the presence of reticulate markings called "netting" on the skin. "Non-netted" or "absence of netting" refers to the fruits lacking such netting.

"Ribbed" refers to grooves and raised parts, running approximately straight and parallel form from (near) blossom end to (near) abscission end that are called "ribs." "Non-ribbed" or "absence of ribbing" refers to the fruits lacking such ribs.

"Cavity" or "seed cavity" refers to the center of the fruit containing the maternal tissues and seeds.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progeny plant, the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Tables 1 and 2 or "all or all but one, two or three of the physiological and morphological characteristics" of Tables 1 and 2.

The physiological and/or morphological characteristics mentioned above are commonly evaluated at significance levels of 1%, 5% or 10% if they are numerical (quantitative), or for having an identical degree (or type) if not numerical (not quantitative), if measured under the same environmental conditions. For example, a progeny plant or a Single Locus Converted plant or a mutated plant of variety NUN 71560 MEM may have one or more (or all) of the essential physiological and/or morphological characteristics of said variety listed in Tables 1 and 2, as determined at the 5% significance level (i.e., $p<0.05$), when grown under the same environmental conditions.

"Distinguishing characteristics" or "distinguishing morphological and/or physiological characteristics" refer herein to the characteristics which distinguish the new variety from other melon varieties, such as the Reference Variety (i.e., are different), when grown under the same environmental conditions. The distinguishing characteristics between melon variety NUN 71560 MEM and the Reference Variety are described herein and can be seed in Table 3. When comparing melon variety NUN 71560 MEM to other varieties, the distinguishing characteristics may be different. In one aspect, the distinguishing characteristics may therefore include one, two, three or more (or all) of the characteristics listed in Tables 1 and 2. All numerical distinguishing characteristics are statistically significantly different at p<0.05 between melon variety NUN 71560 MEM and the other variety (e.g., the Reference Variety).

Melon variety NUN 71560 MEM has the following distinguishing characteristics when compared to the Reference Variety as shown in Table 3, when determined at 5% significance level for numerical characteristics and determined by type or degree for non-numerical characteristics for plants grown under the same environmental conditions.
1. Early maturity cycle;
2. dark green (RHS N137B) mature leaf color;
3. longer mature leaf length;
4. larger mature leaf width;
5. longer mature leaf petiole length;
6. dark intensity of green color of mature leaf;
7. weak leaf blistering;
8. absent or very sparse density of dots of young fruit;
9. small size of dots of young fruit;
10. weak contrast of dot color/ground color of young fruit;
11. medium length of peduncle of young fruit;
12. round shape of fruit at edible maturity;
13. broad diameter of fruit at edible maturity;
14. small to medium ratio of length/diameter of fruit at edible maturity;
15. circular shape in longitudinal section of fruit at edible maturity;
16. medium to large pistil scar of fruit at edible maturity;
17. white rind color (RHS 155A) at edible maturity;
18. yellow green flesh color (RHS 145D) near cavity at edible maturity;
19. yellow green flesh color (RHS 145D) in center at edible maturity;
20. yellow green flesh color (RHS 145D) near rind at edible maturity;
21. higher % soluble solids at edible maturity;
22. less firm flesh (penetrometer reading);
23. larger seed cavity width;
24. medium intensity of cream yellow seed color;
25. no resistance to *Podosphaera xanthii* Race 1;
26. no resistance to *Podosphaera xanthii* Race 2;
27. resistant to *Podosphaera xanthii* Race 5;
28. resistant to *Aphis gossypii*; and
29. resistant to *Fusarium oxysporum* f. sp. *melonis* Race 0.

Thus, a melon plant "comprising the distinguishing characteristics of melon variety NUN 71560 MEM (such as a progeny plant) refers to a plant which does not differ significantly from said variety in the distinguishing characteristics above. Therefore, in one aspect, the disclosure provides a melon plant which does not differ significantly from melon variety NUN 71560 MEM in the distinguishing characteristics above.

Similarity and differences between two different plant lines or varieties can be determined by comparing the number of morphological and/or physiological characteristics (e.g., characteristics as listed in Tables 1 and 2) that are the same (i.e., statistically not significantly different) or that are different (i.e., statistically significantly different) between the two plant lines or varieties using plants grown under the same environmental conditions. A numerical characteristic is considered to be "the same" when the value for a numeric characteristic is not significantly different at the 1% (p<0.01) or 5% (p<0.05) significance level, using T-test, a standard method known to the skilled person. Non-numerical or "degree" or "type" characteristic is considered "the same" when the values have the same "degree" or "type" when scored using USDA and/or UPOV descriptors, if the plants are grown under the same environmental conditions.

In one aspect, a statistical analysis of the quantitative characteristics showing the degree of significance may be provided. Statistical significance is the likelihood that a relationship between two or more variables is caused by something other than chance, i.e., that the differences in the means for quantitative characteristics of the plant of melon variety NUN 71560 MEM and the Reference Variety are significant due to chance. For the purpose of proving differences or distinction between melon variety NUN 71560 MEM and the Reference Variety, a p-value of 5% or 0.05 or lower is considered statistically significant. This means that there is only a 5% probability that the observed result could have happened just by chance or random variation.

The statistical analysis is drawn from a small sample of at least 15 plants or plant parts of melon variety NUN 71560 MEM and the Reference Variety. Statistical points or parameters such as mean, minimum, median, maximum, and standard deviation are collected from the sample data to analyze where the average is, how varied the data set is, and whether the data is skewed. For the purpose of determining whether the result of the data set is statistically significant, a T-Test is used, a statistical tool for proving significance in the means of the two groups (e.g., melon variety NUN 71560 MEM and the Reference Variety) at 5% significance level (a p-value of 5% or 0.05).

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one melon line or variety to another.

"Variety" or "cultivar" means a plant grouping within a single botanical taxon of the lowest rank.

A "plant line" is, for example, a breeding line which can be used to develop one or more varieties. A breeding line is typically highly homozygous.

"Harvested seeds" refer to seeds harvested from a line or variety, e.g., produced after self-fertilization or cross-fertilization and collected.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Locus" (plural loci) refers to the specific location, place or site of a DNA sequence on a chromosome, where, for example, a gene or genetic marker is found. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e., diploid, these chromosomes are referred to as homologous chromosomes, i.e., diploid. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Phenotype" refers to the detectable characteristic of a plant, cell, or organism, which characteristics are the manifestation of gene expression.

"Haploid" refers to a cell or organism having one set of the two sets of chromosomes in a diploid.

"Diploid" refers to a cell or organism having two sets of chromosomes.

"Triploid" refers to a cell or organism having three sets of chromosomes.

"Tetraploid" refers to a cell or organism having four sets of chromosomes.

"Polyploid" refers to a cell or organism having three or more complete sets of chromosomes.

"Tissue culture" or "cell culture" refers to a composition comprising isolated cells of the same or a different type or a collection of such cells organized into parts of a plant. Tissue culture of melon and regeneration of plants therefrom is well known and widely published (see, e.g., Ren et al., In Vitro Cell.Dev.Biol.Plant (2013) 49:223-229; Colijn-Hooymans (1994), Plant Cell, Tissue and Organ Culture 39:211-217). Similarly, methods of preparing cell cultures are known in the art.

"Regeneration" refers to the development of a plant from cell culture or tissue culture or vegetative propagation.

"Vegetative propagation," "vegetative reproduction," or "clonal propagation" are used interchangeably herein and mean a method of taking a plant part and inducing or allowing that plant part to form at least roots, and also refer to the plant or plantlet obtained by that method. Optionally, the vegetative propagation is grown into a mature plant. The skilled person is aware of what plant parts are suitable for use in the method.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 71560 MEM. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another melon plant of the same variety or another variety or line, or with wild melon plants. A progeny may comprise a mutation or a transgene. A "first generation progeny" is the progeny directly derived from, obtained from, obtainable from or derivable from the parent plant by, e.g., traditional breeding methods (selfing and/or cross-pollinating) or regeneration (optionally combined with transformation or mutation). Thus, a plant of variety NUN 71560 MEM is the male parent, the female parent or both of a first generation progeny of melon variety NUN 71560 MEM. Progeny may have all the physiological and morphological characteristics of melon variety NUN 71560 MEM when grown under the same environmental conditions. Using methods such as backcrossing, recurrent selection, mutation or transformation, one or more specific characteristics may be introduced into said variety, to provide or a plant comprising all but 1, 2, or 3 of the morphological and physiological characteristics of melon variety NUN 71560 MEM.

The terms "gene converted" or "conversion plant" or "single locus converted plant" in this context refer to melon plants which are developed by traditional breeding techniques, e.g., backcrossing, or via genetic engineering or through mutation breeding, wherein essentially all of the desired morphological and physiological characteristics of the parent variety or line are recovered, in addition to the one or more characteristics introduced into the parent via e.g., the backcrossing technique (optionally including reverse breeding or reverse synthesis of breeding lines). It is understood that not only the addition of a further characteristic (e.g., addition of gene conferring a further characteristic, such as a disease resistance gene), but also the replacement/modification of an existing characteristic by a different characteristic is encompassed herein (e.g., mutant allele of a gene can modify the phenotype of a characteristic).

Likewise, a "Single Locus Converted (Conversion) Plant" refers to plants developed by plant breeding techniques comprising or consisting of mutation breeding and/or by genetic transformation and/or by traditional breeding techniques, such as backcrossing, wherein essentially all of the desired morphological and physiological characteristics of a melon variety are recovered in addition to the characteristics of the single locus having been transferred into the—variety via abovementioned technique, or wherein the morphological and physiological characteristic of the variety has been replaced/modified in the variety. In case of a hybrid, the gene may be introduced, or modified, in the male or female parental line.

"Transgene" or "chimeric" gene" refers to a genetic locus comprising a DNA sequence which has been introduced into the genome of the plant by transformation. A plant comprising a transgene stably integrated into its genome is referred to as "transgenic plant."

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Average" refers herein to the arithmetic mean.

The term "mean" refers to the arithmetic mean of several measurements. The skilled person understands that the appearance of a plant depends to some extent on the growing conditions of said plant. The mean, if not indicated otherwise within this application, refers to the arithmetic mean of measurements on at least 15 different, randomly selected plants of a variety or line.

DETAILED DESCRIPTION OF THE VARIOUS ASPECTS OF THE DISCLOSURE

The disclosure relates to a plant of variety NUN 71560 MEM, wherein a representative sample of seeds of said variety has been deposited under the Budapest Treaty, with Accession Number NCIMB 44082. NUN 71560 MEM is a Honey Dew melon variety and is suitable for growing in the open field.

In another aspect, melon variety NUN 71560 MEM, or a part thereof, or a progeny thereof, comprises resistance to *Fusarium oxysporum* f. sp. *melonis* Race 2, *Podosphaera xanthii* Race 5, and *Aphis gossypii*, measured according to UPOV standards described in TG/104/5.

The disclosure also provides a melon plant or part thereof having all of the physiological and morphological characteristics of the plant of melon variety NUN 71560 MEM when grown under the same environmental conditions.

The disclosure also provides a plant of variety NUN 71560 MEM, or a part thereof, or a progeny plant thereof, comprising all of the following morphological and/or physiological characteristics (i.e., average values, as indicated on the USDA Objective description of variety-melon (unless indicated otherwise)) as shown in Tables 1 and 2, where the characteristics are determined at the 5% significance level for plants grown under the same environmental conditions. A part of this plant is also provided.

The disclosure further provides a melon plant which does not differ from the physiological and morphological characteristics of the plant of variety NUN 71560 MEM as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant, preferably a fruit or part thereof.

The disclosure further relates to a melon variety NUN 71560 MEM, which when compared to its Reference Variety has the following distinguishing characteristics as shown in Table 3, when determined at 5% significance level for numerical characteristics and determined by type or degree for non-numerical characteristics for plants grown under the same environmental conditions.

1. Early maturity cycle;
2. dark green (RHS N137B) mature leaf color;
3. longer mature leaf length;
4. larger mature leaf width;
5. longer mature leaf petiole length;
6. dark intensity of green color of mature leaf;
7. weak leaf blistering;
8. absent or very sparse density of dots of young fruit;
9. small size of dots of young fruit;
10. weak contrast of dot color/ground color of young fruit;
11. medium length of peduncle of young fruit;
12. round shape of fruit at edible maturity;
13. broad diameter of fruit at edible maturity;
14. small to medium ratio of length/diameter of fruit at edible maturity;
15. circular shape in longitudinal section of fruit at edible maturity;
16. medium to large pistil scar of fruit at edible maturity;
17. white rind color (RHS 155A) at edible maturity;
18. yellow green flesh color (RHS 145D) near cavity at edible maturity;
19. yellow green flesh color (RHS 145D) in center at edible maturity;
20. yellow green flesh color (RHS 145D) near rind at edible maturity;
21. higher % soluble solids at edible maturity;
22. less firm flesh (penetrometer reading);
23. larger seed cavity width;
24. medium intensity of cream yellow seed color;
25. no resistance to *Podosphaera xanthii* Race 1;
26. no resistance to *Podosphaera xanthii* Race 2;
27. resistant to *Podosphaera xanthii* Race 5;
28. resistant to *Aphis gossypii*; and
29. resistant to *Fusarium oxysporum* f. sp. *melonis* Race 0.

The morphological and/or physiological differences between two different individual plants described herein (e.g., between melon variety NUN 71560 MEM and a progeny of said variety) or between a plant of variety NUN 71560 MEM, or progeny of said variety, or a plant having all, or all but 1, 2, or 3, of the physiological and morphological characteristics of melon variety NUN 71560 MEM and another known variety can easily be established by growing said variety under the same environmental conditions (in the same field, optionally next to each other), preferably repeated in several locations which are suitable for cultivation of melons, and measuring the morphological and physiological characteristics of a representative number of plants (e.g., to calculate an average value and to determine the variation range/uniformity within the variety). For example, trials can be carried out in Acampo CA, USA (N 38 degrees 07'261"/W 121 degrees 18' 807", USA), whereby various characteristics, for example, maturity, days from seeding to harvest, plant fertility, plant habit, leaf shape, leaf lobes, leaf color, mature fruit length, mature fruit shape, mature fruit color, blossom scar, shipping quality, ribs presence, fruit abscission, rind net, rind texture, flesh color, flavor, aroma, disease resistance, insect resistance, can be measured and directly compared for species of melon.

Also, at-harvest and/or post-harvest characteristics of fruits can be compared, such as cold storage holding quality, post-harvest flesh firmness, and Brix can be measured using known methods. (Fruit) Flesh firmness can, for example, be measured using a penetrometer, e.g., by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, VA 23502.

Thus, the disclosure comprises a melon plant having one, two, or three physiological and/or morphological characteristics which are different from those of the plant of variety NUN 71560 MEM and which otherwise has all the physiological and morphological characteristics of said variety, e.g., determined at 5% significance level for quantitative characteristics and determined by type or degree for non-quantitative characteristics, when grown under the same environmental conditions. In one aspect, the different characteristic(s) is/are a result of breeding with melon variety NUN 71560 MEM and selection of a progeny plant comprising one, two, or three characteristics which are different than in melon variety NUN 71560 MEM. In another aspect, the different characteristic is the result of a mutation (e.g., spontaneous mutation of a human induced mutation through, e.g., targeted mutagenesis or traditional mutagenesis such as chemically or radiation induced mutagenesis) or it is a result of transformation.

The disclosure also relates to a seed of melon variety NUN 71560 MEM, wherein a representative sample of said seed has been deposited under the Budapest Treaty, with Accession Number NCIMB 44082.

In another aspect, a seed of hybrid variety NUN 71560 MEM is obtainable by crossing the male parent of melon variety NUN 71560 MEM with the female parent of melon variety NUN 71560 MEM and harvesting the seeds produced on the female parent. The resultant seeds of said variety can be grown to produce plants of said variety.

In another aspect, the disclosure provides a plant grown from a seed of melon variety NUN 71560 MEM and plant part thereof.

The disclosure also provides a melon fruit produced on a plant grown from a seed of melon variety NUN 71560 MEM.

In another aspect, the disclosure provides for a plant part of melon variety NUN 71560 MEM, preferably a fruit or part thereof, a representative sample of seed of said melon variety has been deposited under Accession Number NCIMB 44082.

Also provided is a plant of melon variety NUN 71560 MEM, or a fruit or other plant part thereof, produced from a seed, wherein a representative sample of said seeds has been deposited under the Budapest Treaty, with Accession Number NCIMB 44082.

Also provided is a plant part obtained from variety NUN 71560 MEM, wherein said plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, cotyledon, a scion, a stock, a rootstock, a pistil, an anther, and a flower or a part thereof. Such plant parts may be suitable for sexual reproduction (e.g., a pollen, a flower, an ovary, an ovule, an embryo, etc.), vegetative reproduction (e.g., a cutting, a root, a stem, a cell, a protoplast, a leaf, a cotyledon, a meristem, etc.) or tissue culture (e.g., a leaf, a pollen, an embryo, a cotyledon, a hypocotyl, a cell, a root, a root tip, an anther, a flower, a seed, a stem, etc.). Fruits are particularly important plant parts. Fruits may be parthenocarpic, or seedless, or contain immature or nonviable seeds, or contain viable seeds.

In a further aspect, the plant part obtained from melon variety NUN 71560 MEM is a cell, optionally a cell in a cell or tissue culture. That cell may be grown into a plant of variety NUN 71560 MEM. A part of melon variety NUN 71560 MEM (or of a progeny of that variety or of a plant having all physiological and/or morphological characteristics but one, two or three of melon variety NUN 71560 MEM) further encompasses any cells, tissues, organs obtainable from the seedlings or plants in any stage of maturity.

The disclosure also provides a tissue or cell culture comprising cells of melon variety NUN 71560 MEM. Such a tissue culture can, for example, be grown on plates or in liquid culture, or be frozen for long term storage. The cells of melon variety NUN 71560 MEM are used to start the culture can be selected from any plant partsuitable for vegetative reproduction, or in a particular aspect, can be cells of an embryo, meristem, a cotyledon, a hypocotyl, pollen, a leaf, an anther, a root, a root tip, a pistil, a petiole, a flower, a fruit, seed or a stem. In another particular aspect, the tissue culture does not contain somaclonal variation or has reduced somaclonal variation. The skilled person is familiar with methods to reduce or prevent somaclonal variation, including regular reinitiation.

In another aspect, the disclosure provides a melon plant regenerated from the tissue or cell culture of melon variety NUN 71560 MEM, wherein the regenerated plant is not significantly different from melon variety NUN 71560 MEM, in all, or all but one, two or three, of the physiological and morphological characteristics, e.g., determined at 5% significance level for numerical characteristics and determined by type or degree for non-numerical characteristics when grown under the same environmental conditions. Optionally, the plant has one, two, or three of the physiological and morphological characteristics that are affected by a mutation or by transformation. In another aspect, the disclosure provides a melon plant regenerated from the tissue or cell culture of melon variety NUN 71560 MEM, wherein the plant has all of the physiological and morphological characteristics of said variety, e.g., determined at 5% significance level for numerical characteristics and determined by type or degree for non-numerical characteristics when grown under the same environmental conditions. Similarity or difference of a characteristic is determined by measuring that characteristics on a representative number of plants grown under the same environmental conditions, determining whether type/degree characteristics are the same and determining whether numerical characteristics are different at the 5% significance level.

Melon variety NUN 71560 MEM or its progeny, or a plant having all physiological and/or morphological characteristics but one, two or three which are different from those of melon variety NUN 71560 MEM, can also be reproduced using vegetative reproduction methods. Therefore, the disclosure provides for a method of producing a plant, or a plant part, of melon variety NUN 71560 MEM, comprising vegetative propagation of said variety. Vegetative propagation comprises regenerating a whole plant from a plant part of melon variety NUN 71560 MEM, or from a progeny or from or a plant having all physiological and/or morphological characteristics of said variety but one, two, or three different characteristics, such as a cutting, a cell culture, or a tissue culture.

The disclosure also provides methods of vegetatively propagating a part of the plant of the variety NUN 71560 MEM. In certain aspects, the method comprises: (a) cultivating tissue or cells capable of being propagated from melon variety NUN 71560 MEM to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one aspect, the method further comprises step (c) growing plants from said rooted plantlets. Therefore, the method also comprises regenerating a whole plant from a part of the plant of variety NUN 71560 MEM. In a particular aspect, the part of the plant to be propagated is a cutting, a cell culture or a tissue culture.

The disclosure also provides for a vegetatively propagated plant of variety NUN 71560 MEM (or from progeny of melon variety NUN 71560 MEM, or from a plant having all but one, two or three physiological and/or morphological characteristics of melon variety NUN 71560 MEM), wherein the plant has all of the morphological and physiological characteristics of melon variety NUN 71560 MEM, e.g., determined at 5% significance level for numerical characteristics and determined by type or degree for non-numerical characteristics when grown under the same environmental conditions. In another aspect, the propagated plant has all but one, two, or three of the morphological and physiological characteristics of melon variety NUN 71560 MEM, e.g., determined at 5% significance level for numerical characteristics and determined by type or degree for non-numerical characteristics when grown under the same environmental conditions. A part of said propagated plant or said propagated plant with one, two or three differences is also provided. In another aspect, the propagated plant has all or all but 1, 2, or 3 of the physiological and morphological characteristics of melon variety NUN 71560 MEM (e.g., as listed in Tables 1 and 2).

In another aspect, the disclosure provides a method for producing a melon plant part, such as a fruit, comprising growing a plant of variety NUN 71560 MEM until it sets at least one fruit, and collecting the fruit. Preferably, the fruit is collected at harvest maturity. In another aspect, the fruit is collected when the seed is ripe. In a particular aspect, all fruits on a truss can be harvested together. In another particular aspect, all fruit on a melon plant can be harvested at the same time. In other aspects, the disclosure provides for a fruit of melon variety NUN 71560 MEM.

In another aspect, a plant of variety NUN 71560 MEM can be produced by seeding directly in the soil (e.g., the field) or by germinating the seeds in a controlled environment (e.g., greenhouses) and optionally then transplanting the seedlings into the field (see, e.g., Mayberry, et. al., University of California Division of Agriculture and Natural Resources, Publication 7209, 1-3). For example, a seed is sown into a prepared seed bed in a field where the plant remains for its entire life. Alternatively, the melon seed may be planted through a black plastic mulch. The dark plastic will absorb heat from the sun, warming the soil early. It will also help to conserve moisture during the growing season, controls weeds, and makes harvesting easier and cleaner (see, e.g., Hartz et. al., University of California Division of Agriculture and Natural Resources, Publication 7218, 1-4). Melon can also be grown entirely in greenhouses.

In another aspect, the plant and plant parts of melon variety NUN 71560 MEM and progeny of said variety are provided, e.g., grown from seeds, produced by sexual or vegetative reproduction, regenerated from the above-described plant parts, or regenerated from cell or tissue culture of the melon variety NUN 71560 MEM in which the reproduced (seed propagated or vegetatively propagated) plant has all of the physiological and morphological characteristics of melon variety NUN 71560 MEM, e.g., listed in Tables 1 and 2. In one aspect, said progeny of melon variety NUN 71560 MEM can be modified in one, two, or three characteristics, in which the modification is a result of mutagenesis or transformation with a transgene.

In other aspects, the disclosure provides a progeny plant of variety NUN 71560 MEM such as a progeny plant obtained by further breeding with said variety. Further breeding with melon variety NUN 71560 MEM includes selfing that variety and/or cross-pollinating said variety with another melon plant one or more times. In a particular aspect, the disclosure provides for a progeny plant that retains all of the morphological and physiological characteristics of melon variety NUN 71560 MEM, optionally all or all but one, two or three of the characteristics as listed in Tables 1 and 2, determined at the 5% significance level for numerical characteristics, when grown under the same environmental conditions. In another aspect, the progeny is a first generation progeny, i.e., the ovule or the pollen (or both) used in the crossing is an ovule or pollen of melon variety NUN 71560 MEM, where the pollen comes from an anther of melon variety NUN 71560 MEM and the ovule comes from an ovary of melon variety NUN 71560 MEM.

In still another aspect, the disclosure provides a method of producing a melon plant, comprising crossing a plant of variety NUN 71560 MEM with a second melon plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect, the first "crossing" further comprises planting seeds of a first and a second parent melon plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

The disclosure also provides a method for collecting pollen of melon variety NUN 71560 MEM, comprising collecting pollen from a plant of variety NUN 71560 MEM. Alternatively, the method comprises growing plant of variety NUN 71560 MEM until at least one flower of said variety contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a melon flower.

In yet another aspect, the disclosure provides a method of producing a melon plant, comprising selfing melon variety NUN 71560 MEM one or more times, and selecting a progeny melon plant from said selfing. In one aspect, the progeny plant retains all or all but one, two or three of the physiological and morphological characteristics of melon variety NUN 71560 MEM, when grown under the same environmental conditions. In a different aspect, the progeny plant comprises all of the physiological and morphological characteristic of melon variety NUN 71560 MEM of Tables 1 and 2.

The disclosure also provides a method for developing a melon plant in a melon breeding program, using melon variety NUN 71560 MEM, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing melon variety NUN 71560 MEM, or its respective progeny, or a plant comprising all but 1, 2, or 3 or more of the morphological and physiological characteristics of melon variety NUN 71560 MEM (e.g., as listed in Tables 1 and 2) with a different melon plant, and wherein one or more offspring of the crossing are subject to one or more plant breeding techniques: recurrent selection, backcrossing, pedigree breeding, mass selection, mutation breeding and genetic marker enhanced selection (see, e.g., Vidavsky and Czosnek, (1998) Phytopathology 88 (9): 910-4). For breeding methods in general, see, e.g., Principles of Plant Genetics and Breeding, 2007, George Acquaah, Blackwell Publishing, ISBN-13:978-1-4051-3646-4.

In yet another aspect, the disclosure provides for a method of producing a new melon plant comprising crossing a plant of variety NUN 71560 MEM, or a plant comprising all but one, two, or three of the morphological and physiological characteristics of melon variety NUN 71560 MEM (as listed in Tables 1 and 2), or a progeny plant thereof, either as male or as female parent, with a second melon plant (or a wild relative of melon) one or more times, and/or selfing melon plant variety NUN 71560 MEM, or a progeny plant thereof, one or more time, and selecting a progeny melon plant from said crossing and/or selfing. The second melon plant may, for example, be a line or variety of the species *Cucumis melo*, or other *Cucumis* species or even other *Cucurbitacea* species.

In a further aspect, melon variety NUN 71560 MEM is used in crosses with other, different, melon varieties to produce first generation (F1) melon hybrid seeds and plants with superior characteristics. In a particular aspect, the disclosure provides a melon seed and a plant produced by crossing a first parent melon plant with a second parent melon plant, wherein at least one of the first or second parent melon plant is melon variety NUN 71560 MEM. In another aspect, the melon seed and plant produced are the first filial generation (F1) melon seed and plants produced by crossing the plant of melon variety NUN 71560 MEM with another melon plant.

The morphological and physiological characteristics of melon variety NUN 71560 MEM are provided in Tables 1 and 2, as collected in a trial according to USDA and/or UPOV standards. Encompassed herein is also a plant obtainable from melon variety NUN 71560 MEM (e.g., by selfing and/or crossing and/or backcrossing with said variety and/or progeny of said variety) comprising all or all but one, two, or three of the physiological and morphological characteristics of melon variety NUN 71560 MEM listed in Tables 1 and 2, e.g., determined at 5% significance level for numerical characteristics and determined by type or degree for non-numerical characteristics when grown under the same environmental conditions and/or comprising one or more (or all; or all except one, two, or three) characteristics when grown under the same environmental conditions. The morphological and/or physiological characteristics may vary somewhat with variation in the environment (e.g., temperature, light intensity, day length, humidity, soil, fertilizer use, disease vectors), which is why a comparison under the same environmental conditions is preferred. Colors can best be measured using the Royal Horticultural Society (RHS) Chart.

In another aspect, the disclosure provides a method of producing a plant derived from melon variety NUN 71560 MEM, comprising crossing a plant of variety NUN 71560 MEM, either as a male or female parent with a second plant or selfing melon variety NUN 71560 MEM or vegetative reproduction of melon variety NUN 71560 MEM, and collecting seeds from said crossing or selfing or regenerating a whole plant from the vegetable cell- or tissue culture. Also provided are seeds and/or plants obtained by this method. All plants produced using melon variety NUN 71560 MEM as a parent are within the scope of the disclosure, including plant parts derived from melon variety NUN 71560 MEM.

In a further aspect, the method comprises growing a progeny plant of a subsequent generation and crossing the progeny plant of a subsequent generation with itself or a second plant and repeating the steps for additional 3-10 generations to produce a plant derived from melon variety NUN 71560 MEM. The plant derived from melon variety NUN 71560 MEM may be an inbred line and the aforementioned repeating crossing steps may be defined as comprising sufficient inbreeding to produce the inbred line. By selecting plants having one or more desirable traits of the line as well as potentially other selected traits.

The disclosure provides for methods of producing a plant which retain all the morphological and physiological characteristics of the plant described herein. The disclosure also provides for methods of producing a plant comprising all but 1, 2, 3 or more of the morphological and physiological characteristics of melon variety NUN 71560 MEM (e.g., as listed in Tables 1 and 2), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to melon variety NUN 71560 MEM, if its DNA fingerprint is at least 80%, 90%, 95% or 98% identical to the fingerprint of melon variety NUN 71560 MEM. In a particular aspect, AFLP markers are used for DNA fingerprinting (see, e.g., Vos et al. 1995, Nucleic Acid Research 23:4407-4414). A closely related plant may have a Jaccard's Similarity index of at least about 0.8, preferably at least about 0.9, 0.95, 0.98 or more (see, e.g., Parvathaneni et al., J. Crop Sci. Biotech. 2011 (Mar.) 14 (1): 39-43). The disclosure also provides a plant obtained or selected by applying these methods on melon variety NUN 71560 MEM. Such a plant may be produced by traditional breeding techniques, or mutation or transformation or in another aspect, a plant may simply be identified and selected amongst plants of said variety, or progeny of said variety, e.g., by identifying a variant of melon variety NUN 71560 MEM, which variant differs from the variety described herein in one, two or three of the morphological and/or physiological characteristics (e.g., characteristics listed in Tables 1 and 2). In one aspect, the disclosure provides a plant of variety NUN 71560 MEM having a Jaccard's Similarity index with said variety of at least 0.8, e.g., at least 0.85, 0.9, 0.95, 0.98 or even at least 0.99.

In some aspects, the disclosure provides a melon plant comprising genomic DNA having at least 95%, 96%, 97%, 98% or 99% sequence identity compared to the genomic DNA sequence of a plant of variety NUN 71560 MEM as to be deposited under Accession Number NCIMB 44082. In some aspects, the melon plant further comprises all or all but 1, 2, or 3 of the morphological and physiological characteristics of melon variety NUN 71560 MEM (e.g., as listed in Tables 1 and 2). In other aspects, the melon plant is a hybrid derived from a seed or plant of variety NUN 71560 MEM.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48 (3): 443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

In another aspect, the plant of variety NUN 71560 MEM may also be mutated (by e.g., irradiation, chemical mutagenesis, heat treatment, etc.) and mutated seeds or plants may be selected in order to change one or more characteristics of said variety. Methods such as TILLING (Targeting Induced Local Lesions in Genomes) may be applied to populations in order to identify mutants.

Similarly, melon variety NNUN 71560 MEM may be transformed and regenerated, whereby one or more chimeric genes are introduced into the variety or into a plant comprising all but 1, 2, 3, or more of the morphological and physiological characteristics (e.g., as listed in Tables 1 and 2). Many useful traits can be introduced into melon variety NUN 71560 MEM by e.g., crossing melon variety NUN 71560 MEM with a transgenic melon plant comprising a desired transgene, as well as by directly introducing a transgene into melon variety NUN 71560 MEM by genetic transformation techniques.

Any pest or disease resistance genes may be introduced into melon variety NUN 71560 MEM, progeny of said variety or into a plant comprising all but 1, 2, or 3 or more of the morphological and physiological characteristics of melon variety NUN 71560 MEM (e.g., as listed in Tables 1 and 2). Resistance to one or more of the following diseases or pests may be introduced into plants described herein: Bacterial Wilt, Root Rot, Crown Blight, Melon Rust, *Podosphaera xanthii* (*Sphaerotheca fuliginea*) race 1, *Podosphaera xanthii* (*Sphaerotheca fuliginea*) race 2, *Podosphaera xanthii* (*Sphaerotheca fuliginea*) race 3, *Podosphaera xanthii* (*Sphaerotheca fuliginea*) race 5, *Golovinomyces cichoracearum* (*Erysiphe cichoracearum*) race 1, *Verticillum* Wilt, Sulphur Burn, Scab, Downy Mildew, *Fusarium oxysporum* f.sp. *melonis* race 0, *Fusarium oxysporum* f.sp. *melonis* race 1, *Fusarium oxysporum* f.sp. *melonis* race 2, *Fusarium oxysporum* f.sp. *melonis* race 1-2, *Fusarium* Wilt R2, Root Knot (Nematode), Anthracnose, Aphid, Pickle Worm, Darkling Ground Beetle, Banded Cucumber Beetle, Mite, Western Spotted Cucumber Beetle, Melon Leafhopper, Melon Worm, Western Striped Cucumber Beetle and/or Melon Leaf miner. Other resistances, against pathogenic viruses, e.g., Melon Necrotic Spot Virus (MNSV) resistance, Cucumber Mosaic Virus (CMV), Zuchini Yellow Mosaic Virus (ZYMV), *Papaya* Ringspot Virus (PRSV), Watermelon Mosaic Virus (WMV), Squash Mosaic Virus (SMV), Tomato Leaf Curl New Delhi Virus (ToLCNDV)), Cucumber Yellow Stunting Disorder Virus (CYSDV), fungi, bacteria, nematodes, insects, or other pests may also be introduced, or other traits such as Melon Yellowing associated Virus (MYaV) and Whitefly resistances.

Genetic transformation may, therefore, be used to insert a selected transgene into the melon plants of the disclosure described herein or may, alternatively, be used for the preparation of transgenic melon plants which can be used as a source of the transgene(s), which can be introduced into melon variety NUN 71560 MEM by e.g., backcrossing. A genetic trait which has been engineered into the genome of a particular melon plant may then be moved into the genome of another melon plant (e.g., another variety) using traditional breeding techniques which are well known in the art. For example, backcrossing is commonly used to move a transgene from a transformed melon variety into an already developed melon variety and the resulting backcross conversion plant will then comprise the transgene(s).

Any DNA sequences, whether from a different species or from the same species, which are inserted into the genome using transformation, are referred to herein collectively as "transgenes." A "transgene" also encompasses antisense, or sense and antisense sequences capable of gene silencing. Thus, the disclosure also relates to transgenic plants of melon variety NUN 71560 MEM. In some aspects, a transgenic plant of melon variety NUN 71560 MEM may contain at least one transgene but could also contain at least 1, 2, 3, 4, or more transgenes.

Plant transformation involves the construction of an expression vector which will function in plant cells. Such a vector comprises DNA comprising a gene under control of, or operatively linked to a regulatory element active in plant cells (e.g., promoter). The expression vector may contain one or more such operably linked gene/regulatory element combinations. The vector may be in the form of a plasmid and can be used alone or in combination with other plasmids to provide transformed melon plants using transformation methods to incorporate transgenes into the genetic material of the melon plant(s). Transformation can be carried out using standard methods, such as *Agrobacterium tumefaciens* mediated transformation, electroporation, biolistics particle delivery system, or microprojectile bombardment, followed by selection of the transformed cells and regeneration into plants.

Plants can also be genetically engineered, modified, or manipulated to express various phenotypes of horticultural interest. Through the transformation of melon, the expression of genes can be altered to enhance disease resistance, insect resistance, herbicide resistance, stress tolerance, horticultural quality, and other traits. Transformation can also be used to insert DNA sequences which control or help control male sterility or fertility restoration. DNA sequences native to melon as well as non-native DNA sequences can be transformed into melon and used to alter levels of native or non-native proteins. Various promoters, targeting sequences, enhancing sequences, and other DNA sequences can be inserted into the genome for the purpose of altering the expression of proteins. Reduction of the specific activity of specific genes (also known as gene silencing or gene suppression) is desirable for several aspects of genetic engineering in plants.

Genome editing is another method recently developed to genetically engineer plants. Specific modification of chromosomal loci or targeted mutation can be done through sequence-specific nucleases (SSNs) by introducing a targeted DNA double strand break in the locus to be altered. Examples of SSNs that have been applied to plants are: finger nucleases (ZFNs), transcription activator-like effector nucleases (TALENs), engineered homing endonucleases or meganucleases, and clustered regularly interspaced short palindromic repeats (CRISPR)/CRISPR-associated protein 9 (Cas9), see, e.g., Songstad, et. al., Critical Reviews in Plant Sciences, 2017, 36:1, 1-23.

Thus, the disclosure provides a method of producing a melon plant having a desired trait comprising mutating the plant or plant part melon variety NUN 71560 MEM, and selecting a plant comprising the desired trait, wherein the mutated plant contains the desired trait and otherwise retains all or all but one, two or three of the morphological and physiological characteristics of melon variety NUN 71560 MEM, optionally as described for each variety in Tables 1 and 2, and wherein a representative sample of seed of said variety has been deposited under Accession Number NCIMB 44082. In a further aspect, the desired trait is yield, storage properties, color, flavor, size, firmness, enhanced nutritional quality, post-harvest quality, male sterility, herbicide tolerance, insect resistance, pest resistance, disease resistance, environmental stress tolerance, modified carbohydrate metabolism, modified metabolism, or ripening, or the mutation occurs in the intense gene.

The disclosure also provides a method for inducing a mutation in melon variety NUN 71560 MEM, comprising:
 a. exposing the seed, plant or plant part or cell of melon variety NUN 71560 MEM to a mutagenic compound or to radiation, wherein a representative sample of seed of said melon variety has been deposited under Accession Number NCIMB 44082;
b. selecting the seed, plant or plant part or cell of melon variety NUN 71560 MEM having a mutation; and
c. optionally growing and/or multiplying the seed, plant or plant part or cell of melon variety NUN 71560 MEM having the mutation.

The disclosure also provides a method of producing a melon plant having a desired trait, wherein the method comprises transforming the melon plant with a transgene that confers the desired trait, wherein the transformed plant contains the desired trait and otherwise retains all of the physiological and morphological characteristics of the plant of variety NUN 71560 MEM. Thus, a transgenic melon plant is provided which is produced by the method described above, wherein the plant otherwise has all of the physiological and morphological characteristics of the plant of variety NUN 71560 MEM and the desired trait.

In another aspect, the disclosure provides a method of producing a progeny of plant of variety NUN 71560 MEM further comprising a desired trait, said method comprising transforming the plant of melon variety NUN 71560 MEM with at least one transgene that confers the desired trait and/or crossing the plant of melon variety NUN 71560 MEM with a transgenic melon plant comprising a desired transgene so that the genetic material of the progeny that resulted from the cross contains the desired transgene(s). Also encompassed is the progeny produced by this method.

A desired trait (e.g., gene(s) conferring pest or disease resistance, or tolerance for protection, etc.) can be introduced into melon variety NUN 71560 MEM, or progeny of said variety, by transforming said variety or progeny of said variety with a transgene that confers the desired trait, wherein the transformed plant retains all or all but one, two or three of the morphological and/or physiological characteristics of melon variety NUN 71560 MEM, or the progeny of said variety, and contains the desired trait. In another aspect, the transformation or mutation confers a trait wherein the trait is yield, storage properties, color, flavor, size, male sterility, herbicide tolerance, insect resistance, pest resistance, disease resistance, environmental stress tolerance, modified carbohydrate metabolism, modified protein metabolism, ripening, or the mutation occurs in the intense gene. In a particular aspect, the specific transgene may be any known in the art or listed herein, including, a polynucleotide sequence conferring resistance to imidazolinone, sulfonylurea, glyphosate, glufosinate, triazine, benzonitrile, cyclohexanedione, phenoxy proprionic acid and L-phosphinothricin or a polynucleotide conferring resistance to Bacterial Wilt, Root Rot, Crown Blight, Melon Rust, *Podosphaera xanthii* (*Sphaerotheca fuliginea*) race 1, *Podosphaera xanthii* (*Sphaerotheca fuliginea*) race 2, *Podosphaera xanthii* (*Sphaerotheca fuliginea*) race 3, *Podosphaera xanthii* (*Sphaerotheca fuliginea*) race 5, *Golovinomyces cichoracearum* (*Erysiphe cichoracearum*) race 1, Verticillum Wilt, Sulphur Burn, Scab, Downy Mildew, *Fusarium oxysporum* f.sp. *melonis* race 0, *Fusarium oxysporum* f.sp. *melonis* race 1, *Fusarium oxysporum* f.sp. *melonis* race 2, *Fusarium oxysporum* f.sp. *melonis* race 1-2, *Fusarium* Wilt R2, Root Knot (Nematode), Anthracnose, Aphid, Pickle Worm, Darkling Ground Beetle, Banded Cucumber Beetle, Mite, Western Spotted Cucumber Beetle, Melon Leafhopper, Melon Worm, Western Striped Cucumber Beetle and/or Melon Leafminer. Other resistance genes, against pathogenic viruses, e.g., Melon Necrotic Spot Virus (MNSV) resistance, Cucumber Mosaic Virus (CMV), Zuchini Yellow Mosaic Virus (ZYMV), Papaya Ringspot Virus (PRSV), Watermelon Mosaic Virus (WMV), Squash Mosaic Virus (SMV), Tomato Leaf Curl New Delhi Virus (ToLCNDV), Cucumber Yellow Stunting Disorder Virus (CYSDV), fungi, bacteria, nematodes, insects, or other pests may also be introduced, or other traits such as Melon Yellowing associated Virus (MYaV) and Whitefly resistances.

By crossing and/or selfing, (one or more) single traits may be introduced into melon variety NUN 71560 MEM (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into melon variety NUN 71560 MEM by breeding with said variety.

In another aspect, the disclosure provides a method of introducing a single locus conversion or single trait conversion or a desired trait into melon variety NUN 71560 MEM, comprising introducing a single locus conversion, single trait conversion, or a desired trait in at least one of the parents of melon variety NUN 71560 MEM, and crossing the converted parent with the other parent of melon variety NUN 71560 MEM to obtain seed of said variety.

In another aspect, the step of introducing a single locus conversion, single trait conversion, or a desired trait in at least one of the parent plants comprises:
a. crossing the parental line of melon variety NUN 71560 MEM with a second melon plant comprising the single locus conversion, the single trait conversion, or the desired trait;
b. selecting F1 progeny plants that comprise the single locus conversion, the single trait conversion, or the desired trait;
c. crossing said selected progeny plants of step b) with the parental line of step a), to produce a backcross progeny plant;
d. selecting backcross progeny plants comprising the single locus conversion, the single trait conversion, or the desired trait and otherwise all or all but one, two or three of the morphological and physiological characteristics the parental line of step a) to produce selected backcross progeny plants; and
e. optionally repeating steps c) and d) one or more times in succession to produce selected second, third or fourth or higher backcross progeny plants comprising the single locus conversion, the single trait conversion, or the desired trait and otherwise all or all but one, two or three of the morphological and physiological characteristics the parental line of step a) to produce selected backcross progeny plants, when grown in the same environmental conditions.

The disclosure further relates to plants obtained by this method.

Alternatively, a single trait converted plant or single locus converted plant may be produced by:
a. obtaining a cell or tissue culture of cells of melon variety NUN 71560 MEM;
b. genetically transforming or mutating said cells;
c. growing the cells into a plant; and
d. optionally selecting the plant that contains the single locus conversion, the single trait conversion, or the desired trait.

In another aspect, the disclosure provides a method of introducing a single locus conversion or single trait conversion or a desired trait into melon variety NUN 71560 MEM, comprising:
a. obtaining a combination of a parental lines of melon variety NUN 71560 MEM, optionally through reverse synthesis of breeding lines;
b. introducing a single locus conversion, a single trait conversion, or a desired trait in at least one of the parents of step a); and
c. crossing the converted parent with the other parent of step a) to obtain seed of melon variety NUN 71560 MEM.

In another method, the step of introducing a single locus conversion, single trait conversion, or a desired trait in at least one of the parents comprises genetically transforming or mutating cells the parental line of melon variety NUN 71560 MEM, growing the cells into a plant; and optionally selecting plants that contain the single locus conversion, the single trait conversion, or the desired trait.

In any of the above methods, where the single locus conversion concerns a trait, the trait may be yield or pest resistance or disease resistance. In one aspect, the trait is disease resistance and the resistance is conferred to Bacterial Wilt, Root Rot, Crown Blight, Melon Rust, *Podosphaera xanthii* (*Sphaerotheca fuliginea*) race 1, *Podosphaera xanthii* (*Sphaerotheca fuliginea*) race 2, *Podosphaera xanthii* (*Sphaerotheca fuliginea*) race 3, *Podosphaera xanthii* (*Sphaerotheca fuliginea*) race 5, *Golovinomyces cichoracearum* (*Erysiphe cichoracearum*) race 1, *Verticillum* Wilt, Sulphur Burn, Scab, Downy Mildew, *Fusarium oxysporum* f.sp. *melonis* race 0, *Fusarium oxysporum* f.sp. *melonis* race 1, *Fusarium oxysporum* f.sp. *melonis* race 2, *Fusarium oxysporum* f.sp. *melonis* race 1-2, *Fusarium* Wilt R2, Root Knot (Nematode), Anthracnose, Aphid, Pickle Worm, Darkling Ground Beetle, Banded Cucumber Beetle, Mite, Western Spotted Cucumber Beetle, Melon Leafhopper, Melon Worm, Western Striped Cucumber Beetle and/or Melon Leafminer. Other resistances, against pathogenic viruses, e.g., Melon Necrotic Spot Virus (MNSV) resistance, Cucumber Mosaic Virus (CMV), Zuchini Yellow Mosaic Virus (ZYMV), *Papaya* Ringspot Virus (PRSV), Watermelon Mosaic Virus (WMV), Squash Mosaic Virus (SMV), Tomato Leaf Curl New Delhi Virus (ToLCNDV), Cucumber Yellow Stunting Disorder Virus (CYSDV), fungi, bacteria, nematodes, insects, or other pests may also be introduced, or other traits such as Melon Yellowing associated Virus (MYaV) and Whitefly resistances.

The disclosure also provides a plant having one, two, or three physiological and/or morphological characteristics which are different from those of melon variety NUN 71560 MEM and which otherwise has all the physiological and morphological characteristics of said variety, wherein a representative sample of seed of said melon variety has been deposited under Accession Number NCIMB 44082. In particular, variants are encompassed which differ from melon variety NUN 71560 MEM in none, one, two, or three of the characteristics mentioned in Tables 1 and 2 are encompassed.

The disclosure also provides a plant comprising at least a first set of the chromosomes of melon variety NNUN 71560 MEM, a sample of seed has been deposited under Accession Number NCIMB 44082, optionally further comprising a single locus conversion. In another aspect, the single locus conversion confers a trait wherein the trait is yield, storage properties, color, flavor, size, firmness, enhanced nutritional quality, post-harvest quality, male sterility, herbicide tolerance, insect resistance, pest resistance, disease resistance, environmental stress tolerance, modified carbohydrate metabolism, modified metabolism, or ripening.

In another aspect, the disclosure provides a haploid plant and/or a doubled haploid plant of melon variety NUN 71560 MEM, or a plant having all but one, two or three physiological and/or morphological characteristics of melon variety NUN 71560 MEM, or progeny of any of the variety. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with a chromosome doubling agent and regenerating the cells or tissues into a whole plant.

In another aspect, the disclosure comprises a method for making doubled haploid cells of melon variety NUN 71560 MEM, comprising making doubled haploid cells from haploid cells from the plant or plant part of melon variety NUN 71560 MEM with a chromosome doubling agent such as colchicine treatment (see, e.g., Nikolova and Niemirowicz-Szczytt (1996) Acta Soc Bot Pol 65:311-317).

In another aspect, the disclosure provides for haploid plants and/or doubled haploid plants derived from melon variety NUN 71560 MEM that, when combined, make a set of parents of melon variety NUN 71560 MEM. The haploid plant and/or the doubled haploid plant of variety NUN 71560 MEM can be used in a method for generating parental lines of melon variety NUN 71560 MEM.

The disclosure also provides methods for determining the identity of parental lines of plants described herein, in particular the identity of the female line. US2015/0126380, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of variety NUN 71560 MEM, or is a progeny of said variety, because the seed coat of the seed is a maternal tissue genetically identical to melon variety NUN 71560 MEM. In one aspect, the disclosure relates to a maternal tissue of melon variety NUN 71560 MEM. In another aspect, the disclosure relates to a melon seed comprising a maternal tissue of melon variety NUN 71560 MEM. In another particular aspect, the disclosure provides a method of identifying the female parental line of melon variety NUN 71560 MEM by analyzing the seed coat of a seed of that variety. In another aspect, the skilled person can determine whether a seed is grown on melon variety NUN 71560 MEM by analyzing the seed coat or another maternal tissue of said seed.

Using methods known in the art such as "reverse synthesis of breeding lines" or "reverse breeding", it is possible to produce parental lines for a hybrid plant such as melon variety NUN 71560 MEM. A skilled person can take any individual heterozygous plant (called a "phenotypically superior plant" in Example 2 of US2015/0245570 hereby incorporated by reference in its entirety; melon variety NUN 71560 MEM is such plant) and generate a combination of parental lines (reverse breeding parental lines) that, when crossed, produce the variety NUN 71560 MEM. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US2015/0245570 or from Wijnker et al., Nature Protocols Volume: 9, Pages: 761-772 (2014) DOI:doi: 10.1038/nprot.2014.049. Thus, the disclosure provides a method for producing parental lines for a hybrid organism (e.g., melon variety NUN 71560 MEM), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of melon variety NUN 71560 MEM, which when crossed reconstitute the genome of melon variety NUN 71560 MEM, comprising:
  a. defining a set genetic markers that are present a heterozygous form (H) in a partially heterozygous starting organism;
  b. producing at least one further generation from the starting organism by self-pollination (e.g., F2 or F3 generation);
  c. selecting at least one pair of progeny organisms in which at least one genetic marker from the set is present in a complementary homozygous form (B vs. A, or A vs. B); and
  d. optionally repeating steps b) and c) until at least one pair of progeny organisms that have complementary alleles for at least a subset of the genetic markers has been selected as parental lines for a hybrid.

The disclosure relates to a method of producing a combination of parental lines of a plant of variety NUN 71560 MEM, comprising making doubled haploid cells from haploid cells from said plant or a seed of that plant; and optionally crossing these parental lines to produce and collecting seeds. In another aspect, the disclosure relates to a combination of parental lines produced by this method. In still another aspect, the combination of parental lines can be used to produce a seed or plant of variety NUN 71560 MEM, when these parental lines are crossed. In still another aspect, the disclosure relates to a combination of parental lines from which a seed or plant having all physiological and/or morphological characteristics of melon variety NUN 71560 MEM (when the characteristics are determined at the 5% significance level for plants grown under the same conditions).

The disclosure also provides a combination of parental lines which, when crossed, produce a seed or plant having all physiological and/or morphological characteristics of melon variety NUN 71560 MEM, but one, two, or three characteristics which are different (when grown under the same environmental conditions), as well as a seed or plant having all physiological and/or morphological characteristics of melon variety NUN 71560 MEM, but one, two, or three characteristics which are different (when the numerical characteristics are determined at the 5% significance level for plants and determined by type or degree for non-numerical characteristics, when grown under the same conditions).

In another aspect, a combination of a male and a female parental line of NUN 71560 MEM can be generated by methods described herein, for example, through reverse synthesis of breeding lines.

In another aspect, the disclosure provides a method of determining the genotype of a plant described herein comprising detecting in the genome (e.g., a sample of nucleic acids) of the plant at least a first polymorphism or an allele. The skilled person is familiar with many suitable methods of genotyping, detecting a polymorphism or detecting an allele including SNP (Single Nucleotide Polymorphism) genotyping, restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example, by obtaining a sample of nucleic acid from a plant and detecting in said nucleic acids a plurality of polymorphisms. The method may further comprise storing the results of the step of detecting the plurality of polymorphisms on a computer readable medium.

Also provided is a plant part obtained from variety NUN 71560 MEM (or from progeny of said variety or from a plant having all or all but one, two, or three of the physiological and morphological characteristics which are different from those of melon variety NUN 71560 MEM or from a vegetatively propagated plant of variety NUN 71560 MEM, or from its progeny or from a plant having all or all but one, two, or three of the physiological and morphological characteristics which are different from those of melon variety NUN 71560 MEM), wherein said plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, cotyledon, a scion, a stock, a rootstock, a pistil, an anther, and a flower or a part thereof.

A part of the plant of variety NUN 71560 MEM (or of progeny of said variety or of a plant having all of the physiological and/or morphological characteristics but one, two or three which are different from those of said variety) encompasses any cells, tissues, organs obtainable from the seedlings or plants, such as but not limited to: a melon fruit or a part thereof, a cutting, a hypocotyl, a cotyledon, seed coat, or pollen. Such a plant part of melon variety NUN 71560 MEM can be stored and/or processed further.

The disclosure thus also provides for a food or a feed product comprising one or more of such parts from melon variety NUN 71560 MEM, or from progeny of said variety, or from a derived variety, such as a plant having all but one, two or three physiological and/or morphological characteristics of melon variety NUN 71560 MEM. Preferably, the plant part is a melon fruit or part thereof and/or an extract from a fruit or another plant part described herein comprising at least one cell of melon variety NUN 71560 MEM. The food or feed product may be fresh or processed, e.g., dried, grinded, powdered, pickled, chopped, cooked, roasted, in a sauce, in a sandwich, pasted, puréed or concentrated, juiced, sliced, canned, steamed, boiled, fried, blanched or frozen, etc.

In another aspect, the disclosure provides for a melon fruit of variety NUN 71560 MEM, or part of a fruit of said variety. The fruit can be in any stage of maturity, for example, immature or mature. In another aspect, the disclosure provides for a container comprising or consisting of a plurality of harvested melon fruits or parts of fruits of said variety, or fruits of progeny thereof, or fruits of a derived variety.

Marketable fruits are generally sorted by size and quality after harvest. Alternatively, the fruits can be sorted by expected shelf life, pH or Brix.

In another aspect, the plant, plant part or seed of melon variety NUN 71560 MEM is inside one or more containers. For example, the disclosure provides containers such as cans, boxes, crates, bags, cartons, Modified Atmosphere Packaging, films (e.g., biodegradable films), etc. comprising a plant or part of a plant (fresh and/or processed) or a seed of melon variety NUN 71560 MEM. In a particular aspect, the container comprises a plurality of seeds of melon variety NUN 71560 MEM, or a plurality of plant parts of melon variety NUN 71560 MEM. The seed may be disinfected, primed and/or treated with various compounds, such as seed coatings or crop protection compounds. The seed produces a plant of variety NUN 71560 MEM.

Melons may also be grown for use as rootstocks (stocks) or scions. Typically, different types of melons are grafted to enhance disease resistance, which is usually conferred by the rootstock, while retaining the horticultural qualities usually conferred by the scion. It is not uncommon for grafting to occur between cultivated melon varieties and related melon species. Methods of grafting and vegetative propagation are well-known in the art.

In another aspect, the disclosure provides to a plant comprising a rootstock or scion of melon variety NUN 71560 MEM.

All documents (e.g., patent publications) are herein incorporated by reference in their entirety, including the following cited references:

Naktuinbow, Calibration book *Cucumis melo* L., world-wide web at naktuinbow.nl.

US Department of Agriculture, Objective Description of Variety-Muskmelon/Cantaloupe (*Cucumis melo* L.)", world-wide web at ams.usda.gov/under services/plant-variety-protection/pvpo-c-forms under muskmelon.

UPOV, Guidelines for the Conduct of Tests for Distinctness, Uniformity and Stability, TG104/5, world-wide web at upov.int/edocs/tgdocs/en/tg104.pdf.

Colijn-Hooymans, J. C., et. al., "Competence for Regeneration of Cucumber Cotyledons is Restricted to Specific Developmental Stages", Plant Cell, Tissue and Organ Culture, 1994, vol. 39, pp. 211-217.

Hartz, T., et. al, "Cantaloupe Production in California," University of California Division of Agriculture and Natural Resouces, Vegetable Production Series, Publication 7218, pp. 1-4.

Mayberry, K., et. al., "Mized Melon Production in California," University of California Division of Agriculture and Natural Resouces, Vegetable Production Series, Publication 7209, pp. 1-3.

Needleman, S. B., et. al., "A General Method Applicable to the Search for Similarities in the Amino Acid Sequence of Two Proteins", Journal of Molecular Biology, 1970, vol. 48 (3), pp. 443-53.

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Parvathaneni, R. K., et al., "Fingerprinting in Cucumber and Melon (*Cucumis* spp.) genotypes Using Morphological and ISSR Markers", Journal of Crop Science and Biotechnology, 2011, vol. 14, no. 1, pp. 39-43. DOI No. 10.1007/s12892-010-0080-1.

Rice, P., et al., "EMBOSS: The European Molecular Biology Open Software Suite", Trends in Genetics, 2000, vol. 16, Issue 6. pp. 276-277.

Ren, Y., et al., "Shoot Regeneration and Ploidy Variation in Tissue Culture of Honeydew Melon (*Cucumis melo* L. *inodorus*)", In Vitro Cellular & Development Biology-Plant, 2013, vol. 49, p. 223-229.

Vidavsky, F., et. al., "Tomato Breeding Lines Resistant and Tolerant to Tomato Yellow Leaf Curl Virus Issued from *Lycopersicum hirsutum*", The American Phytopathology Society, 1998, vol. 88, no. 9, pp. 910-914.

Vos, P., et al., AFLP: A New Technique for DNA Fingerprinting 1995, Nucleic Acids Research, 1995, vol. 23, No. 21, pp. 4407-4414.

Wijnker, E., et al., Hybrid Recreation by Reverse breeding in *Arabidopsis thaliana*, Nature Protocols, 2014, vol. 9, pp. 761-772. DOI: doi: 10.1038/nprot.2014.049

U.S. Pat. No. 10,334,797

US 2015/0126380

US 2015/0245570

US 2017/0071145

US 2017/0240913

US 2017/0335339

Development of Melon Variety NUN 71560 MEM

The hybrid variety NUN 71560 MEM was developed from a male and female proprietary inbred line of Nunhems. The female and male parents were crossed to produce hybrid (F1) seeds of melon variety NUN 71560 MEM. The seeds of melon variety NUN 71560 MEM can be grown to produce hybrid plants and parts thereof (e.g., melon fruit). The hybrid variety NUN 71560 MEM can be propagated by seeds or vegetatively.

The hybrid variety is uniform and genetically stable. This has been established through evaluation of horticultural characteristics. Several hybrid seed production events resulted in no observable deviation in genetic stability. Coupled with the confirmation of genetic stability of the respective female and male parents the Applicant has concluded that melon variety NUN 71560 MEM is uniform and stable.

Deposit Information

A total of 625 seeds of the hybrid variety NUN 71560 MEM was made and accepted according to the Budapest Treaty by Nunhems B. V. on Nov. 29, 2022 at the NCIMB Ltd., Ferguson Building, Craibstone Estate, Bucksburn, Aberdeen AB21 9YA, United Kingdom (NCIMB). The deposit has been assigned Accession Number NCIMB 44082. A statement indicating the viability of the sample has been provided. A deposit of melon variety NUN 71560 MEM and of the male and female parent line is also maintained at Nunhems B. V. The seed lot number for melon variety NUN 71560 MEM is 32480201002.

The deposit will be maintained in NCIMB for a period of 30 years, or 5 years after the most recent request, or for the enforceable life of the patent whichever is longer and will be replaced if it ever becomes nonviable during that period. Access to the deposits will be available during the pendency of this application to persons determined by the Director of the U.S. Patent Office to be entitled thereto upon request.

Subject to 37 C.F.R. § 1.808 (b), all restrictions imposed by the depositor on the availability to the public of the deposited material will be irrevocably removed upon the granting of the patent. Applicant does not waive any rights granted under this patent on this application or under the Plant Variety Protection Act (7 U.S.C. § 2321 et seq.). Accordingly, the requirements of 37 CFR § 1.801-1.809 have been satisfied.

Characteristics of Melon Variety NUN 71560 MEM

The most similar variety to NUN 71560 MEM refers to variety Summer Dew, a commercial variety from Harris Moran.

In Tables 1 and 2, a comparison between melon variety NUN 71560 MEM and the Reference Variety are shown based on a trial in the USA under open field conditions. Trial location: Acampo, California, USA; Harvesting date: Aug. 19, 2022. In Table 3, the distinguishing characteristics between melon variety NUN 71560 MEM and the Reference Variety are shown.

One replication of 20 plants per variety, from which at least 15 plants or plant parts were randomly selected and were used to measure the characteristics. For numerical characteristics, averages were calculated. For non-numerical characteristics, the type/degree were determined. Similarity and differences between two different plant lines or varieties can be determined by comparing the number of morphological and/or physiological characteristics (e.g., characteristics as listed in Tables 1 and 2) that are the same (i.e., statistically not significantly different) or that are different (i.e., statistically significantly different) between the two plant lines or varieties using plants grown under the same environmental conditions. A numerical characteristic is considered to be "the same" when the value for a numeric characteristic is not significantly different at the 1% (p<0.01) or 5% (p<0.05) significance level, using T-test, a standard method known to the skilled person. Non-numerical or "degree" or "type" characteristic is considered "the same" when the values have the same "degree" or "type" when scored using USDA and/or UPOV descriptors, for plants are grown under the same environmental conditions. In one aspect, a statistical analysis using the T-Test at 5% significance level is provided (see, Tables 4-18).

In another aspect, the disclosure provides a plant having the physiological and morphological characteristics of melon variety NUN 71560 MEM as presented in Tables 1 and 2 when grown under the same environmental conditions, wherein a representative sample of seed of said melon variety is deposited under Accession Number NCIMB 44082.

TABLE 1

Objective Description of Melon Variety NUN 71560 MEM and the Reference Variety (USDA Descriptors) based on California, USA Trial, 2022

| Characteristics | Application Variety (NUN 71560 MEM) | Reference Variety (Summer Dew) |
|---|---|---|
| Type: Persian; Honey Dew; Casaba; Crenshaw; Common/Summer; Other | Honey Dew | Honey Dew |
| Area of best adaptation: | Most areas | Most areas |
| Maturity: | | |
| Days from seeding to harvest | 80 days | 90 days |
| Maturity cycle: | Early | Late |
| Plant: | | |
| Fertility: andromonoecious, monoecious, gynoecious, other | Andromonoecious | Andromonoecious |
| Habit: vine, semi-bush, bush | Vine | Vine |
| Vigor: | Strong | Strong |
| Leaf (mature blade of third leaf): | | |
| Shape: orbicular, ovate, reniform | Reniform | Reniform |
| Lobes: not lobed, shallowly lobed, deeply lobed | Shallowly lobed | Shallowly lobed |
| Color: light green, medium green, dark green | Dark green RHS N137B | Dark green N137A |
| Length (cm): | 16.21 cm | 14.03 cm |
| Width (cm): | 15.77 cm | 14.13 cm |
| Surface: pubescent, glabrous, scabrous | Scabrous | Scabrous |
| Fruit (at edible maturity): | | |
| Length (cm): | 16.47 cm | 17.15 cm |
| Diameter (cm): | 23.44 cm | 15.25 cm |
| Weight (kg): | 1.76 kg | 1.89 kg |
| Shape: oblate, round, elongate-cylindrical, spindle, acorn | Round | Oval |
| Surface: smooth, netted, corrugated, warted | Smooth | Smooth |
| Blossom Scar: obscure, conspicuous | Conspicuous | Conspicuous |
| Rib Presence: absent, present | Absent | Absent |

TABLE 1-continued

Objective Description of Melon Variety NUN 71560 MEM and the Reference Variety (USDA Descriptors) based on California, USA Trial, 2022

| Characteristics | Application Variety (NUN 71560 MEM) | Reference Variety (Summer Dew) |
|---|---|---|
| Ribs Surface: smooth, netted | Smooth | Smooth |
| Suture Depth: shallow, medium, deep | Shallow | Shallow |
| Suture Surface: smooth, netted | Smooth | Smooth |
| Shipping Quality: poor, fair, excellent | Excellent | Excellent |
| Fruit Abscission: when ripe, when overripe, do not abscise | Does not abscise | Does not abscise |
| Rind Net: | | |
| Net Presence: absent, sparse, abundant | Absent | Absent |
| Rind Texture: | | |
| Texture: soft, firm, hard | Hard | Hard |
| Thickness at Medial (mm): | 44.28 mm | 45.47 mm |
| Rind Color: white, cream, buff, yellow, gold, green, orange, bronze, brown, gray, black, other | | |
| Rind Color (at edible maturity): | | |
| Primary color: | White RHS 155A | White RHS 157A |
| Flesh (at edible maturity): white, cream, yellow, green, orange, salmon, pink, other | | |
| Color Near Cavity: | Yellow green RHS 145D | Yellow green RHS 145C |
| Color in Center: | Yellow green RHS 145D | Yellow green RHS 144A |
| Color Near Rind: | Yellow green RHS 145D | Yellow green RHS 144A |
| Refractometer % Soluble Solids (Center of Flesh): | 15.37% | 10.34% |
| Aroma: absent, faint, strong | Absent | Absent |
| Flavor: mild, somewhat spicy, very spicy | Mild | Mild |
| Seed Cavity: | | |
| Length (mm): | 101.61 mm | 105.35 |
| Width (mm): | 61.09 mm | 69.84 mm |
| Shape in X-Section: circular, triangular | Triangular | Triangular |
| Disease Resistances: | | |
| *Fusarium oxysporum* f. sp. *melonis* Race 0 | Susceptible | Highly resistant |
| *Fusarium oxysporum* f. sp. *melonis* Race 2 | Intermediately resistant | Highly resistant |
| *Podosphaera xanthii* Race 1 | Absent | Intermediately resistant |
| *Podosphaera xanthi* Race 2 | Absent | Intermediately resistant |
| *Podosphaera xanthii* Race 5 | Intermediately resistant | Absent |
| *Aphis gossypii* | Intermediately resistant | Absent |

TABLE 2

Objective Description of Melon variety NUN 71560 MEM and the Reference Variety (Non-USDA Descriptors) based on California, USA Trial, 2022

| Characteristics | Application Variety (NUN 71560 MEM) | Reference Variety (Summer Dew) |
|---|---|---|
| Leaf (mature blade of 3$^{rd}$ leaf): | | |
| Size: very small, very small to small, small, small to medium, medium, medium to large, large, large to very large, very large | Medium | Medium |
| Intensity of green color: very light, very light to light, light, light to medium, medium, medium to dark, dark, dark to very dark, very dark | Dark | Dark to very dark |
| Development of lobes: very weak, very weak to weak, weak, weak to medium, medium, medium to strong, strong, strong to very strong | Medium | Medium |
| Length of terminal lobe: very short, very short to short, short, short to medium, medium, medium to long, long, long to very long, very long | Short | Short |
| Dentation of margin: very weak, very weak to weak, weak, weak to medium, medium, medium to strong, strong, strong to very strong, very strong | Weak | Weak |
| Blistering: very weak, very weak to weak, weak, weak to medium, medium, medium to strong, strong, strong to very strong, very strong | Weak | Weak to medium |
| Petiole attitude: erect, erect to semi-erect, semi-erect, semi-erect to horizontal, horizontal | Erect | Erect |
| Petiole length: very short, very short to short, short, short to medium, medium, medium to long, long, long to very long, very long | Long | Medium |
| Petiole length, cm: | 18.44 cm | 14.73 cm |
| Petiole width, mm: | 5.72 mm | 5.65 mm |
| Young fruit (unripe fruit, before the color change): | | |
| Hue of green color of skin: whitish green, yellowish green, green, greyish green | Greyish green | Greyish green |
| Intensity of green color of skin: very light, very light to light, light, light to medium, medium, medium to dark, dark, dark to very dark, very dark | Light | Light |
| Density of dots: absent or very sparse, very sparse, sparse, sparse to medium, medium, medium to dense, dense, dense to very dense, very dense | Absent or very sparse | Medium |
| Size of dots: very small, very small to small, small, small to medium, medium, medium to large, large, large to very large, very large | Small | Very small |
| Contrast of dot color/ground color: very weak, very weak to weak, weak, weak to medium, medium, medium to strong, strong, strong to very strong, very strong | Weak | Medium |
| Conspicuousness of groove coloring: absent or very weak, very weak to weak, weak, weak to medium, medium, medium to strong, strong, strong to very strong | Absent or very weak | Absent or very weak |
| Intensity of Groove Coloring: very light, very light to light, light, light to medium, medium, medium to dark, dark, dark to very dark, very dark | Light | Very light |
| Length of peduncle: very short, very short to short, short, short to medium, medium, medium to long, long, long to very long, very long | Medium | Long |

TABLE 2-continued

Objective Description of Melon variety NUN 71560 MEM and the Reference Variety (Non-USDA Descriptors) based on California, USA Trial, 2022

| Characteristics | Application Variety (NUN 71560 MEM) | Reference Variety (Summer Dew) |
|---|---|---|
| Length of peduncle, mm: | 28.39 mm | 29.73 mm |
| Thickness of peduncle 1 cm from fruit: very thin, very thin to thin, thin, thin to medium, medium, medium to thick, thick to very thick, very thick | Medium | Medium |
| Thickness of peduncle, mm: | 7.54 mm | 7.93 mm |
| Extension of darker area around peduncle: absent or very small, very small to small, small, small to medium, medium, medium to large, large, large to very large | Absent or very small | Absent or very small |
| Young fruit ground color: | Yellow green | Yellow green |
| Young fruit dot color: | Yellow green | Yellow green |
| Fruit (at edible maturity): | | |
| Fruit length: very short, very short to short, short, short to medium, medium, medium to long, long, long to very long, very long | Medium | Medium |
| Diameter: very narrow, very narrow to narrow, narrow, narrow to medium, medium, medium to broad, broad, broad to very broad, very broad | Broad | Medium |
| Ratio of length/diameter: very small, very small to small, small, small to medium, medium, medium to large, large, large to very large, very large | Small to medium | Medium |
| Ratio of length/diameter: | 0.70 | 1.12 |
| Position of maximum diameter: toward stem end, at middle, toward blossom end | At middle | At middle |
| Shape in longitudinal section: ovate, medium elliptic, broad elliptic, circular, quadrangular, oblate, obovate, elongated | Circular | Broad elliptic |
| Ground color of skin: white, yellow, green, grey, | White | White |
| Intensity of ground color of skin: very light, very light to light, light, light to medium, medium, medium to dark, dark, dark to very dark, very dark | Light | Light |
| Hue of ground color of skin: absent or very weak, whitish, yellowish, orange, ochre, greenish, greyish | Whitish | Whitish |
| Density of dots: absent or very sparse, very sparse, sparse, sparse to medium, medium, medium to dense, dense, dense to very dense, very dense | Medium | Medium |
| Size of dots: very small, very small to small, small, small to medium, medium, medium to large, large, large to very large, very large | Very small | Very small |
| Color of dots: white, yellow, green | White | White |
| Intensity of color of dots: very light, very light to light, light, light to medium, medium, medium to dark, dark, dark to very dark, very dark | Light | Light |
| Density of patches: absent or very sparse, very sparse, sparse, sparse to medium, medium, medium to dense, dense, dense to very dense, very dense | Absent or very sparse | Absent or very sparse |
| Warts: absent, present | Absent | Absent |
| Strength of attachment of peduncle at maturity: very weak, very weak to weak, weak, weak to medium, medium, medium to strong, strong, strong to very strong, very strong | Medium | Medium |
| Shape of base: pointed, rounded, truncate | Rounded | Rounded |

TABLE 2-continued

Objective Description of Melon variety NUN 71560 MEM and the Reference Variety (Non-USDA Descriptors) based on California, USA Trial, 2022

| Characteristics | Application Variety (NUN 71560 MEM) | Reference Variety (Summer Dew) |
|---|---|---|
| Shape of apex: pointed, rounded, truncate | Rounded | Rounded |
| Size of pistil scar: very small, very small to small, small, small to medium, medium, medium to large, large, large to very large, very large | Medium to large | Medium |
| Grooves: absent or weakly expressed, weakly expressed, strongly expressed | Absent or weakly expressed | Absent or weakly expressed |
| Creasing of surface: absent or very weak, very weak to weak, weak, weak to medium, medium, medium to strong, strong, strong to very strong | Absent or very weak | Absent or very weak |
| Cork formation: absent, present | Absent | Absent |
| Width of flesh in longitudinal section (at position of maximum fruit diameter): very thin, very thin to thin, thin, thin to medium, medium, medium to thick, thick to very thick, very thick | Medium to thick | Medium to thick |
| Blossom scar diameter, mm: | 15.76 mm | 14.85 mm |
| Secondary color of skin: absent, present | Present | Present |
| Distribution of secondary color of skin: in dots, in spots, in dots and in spots | In dots | In dots |
| Fruit size uniformity: | Good | Good |
| Ease of harvest: | Easy | Easy |
| Flesh (at edible maturity): | | |
| Penetrometer, kg: | 3.7 kg | 4.68 kg |
| Internal cavity: | Open | Very open |
| Seeds: | | |
| Seed color: whitish, creamy yellow | Cream yellow | Cream yellow |
| Intensity of seed color: | Medium | Medium to dark |

TABLE 3

Distinguishing Characteristics between Melon variety NUN 71560 MEM and the Reference Variety

| Characteristics | Application Variety (NUN 71560 MEM) | Reference Variety (Summer Dew) |
|---|---|---|
| Maturity: | | |
| Maturity cycle: | Early | Late |
| Leaf (mature blade of $3^{rd}$ leaf): | | |
| Color: light green, medium green, dark green | Dark green RHS N137B | Dark green N137A |
| Length (cm): | 16.21 cm | 14.03 cm |
| Width (cm): | 15.77 cm | 14.13 cm |
| Petiole length: very short, very short to short, short, short to medium, medium, medium to long, long, long to very long, very long | Long | Medium |
| Petiole length, cm: | 18.44 cm | 14.73 cm |
| Intensity of green color: very light, very light to light, light, light to medium, medium, medium to dark, dark, dark to very dark, very dark | Dark | Dark to very dark |
| Blistering: very weak, very weak to weak, weak, weak to medium, medium, medium to strong, strong, strong to very strong, very strong | Weak | Weak to medium |

TABLE 3-continued

Distinguishing Characteristics between Melon variety NUN 71560 MEM and the Reference Variety

| Characteristics | Application Variety (NUN 71560 MEM) | Reference Variety (Summer Dew) |
|---|---|---|
| Young fruit (unripe fruit, before the color change): | | |
| Density of dots: absent or very sparse, very sparse, sparse, sparse to medium, medium, medium to dense, dense, dense to very dense, very dense | Absent or very sparse | Medium |
| Size of dots: very small, very small to small, small, small to medium, medium, medium to large, large, large to very large, very large | Small | Very small |
| Contrast of dot color/ground color: very weak, very weak to weak, weak, weak to medium, medium, medium to strong, strong, strong to very strong, very strong | Weak | Medium |
| Length of peduncle: very short, very short to short, short, short to medium, medium, medium to long, long, long to very long, very long | Medium | Long |
| Fruit (at edible maturity): | | |
| Shape: oblate, round, elongate-cylindrical, spindle, acorn | Round | Oval |
| Diameter: very narrow, very narrow to narrow, narrow, narrow to medium, medium, medium to broad, broad, broad to very broad, very broad | Broad | Medium |
| Ratio of length/diameter: very small, very small to small, small, small to medium, medium, medium to large, large, large to very large, very large | Small to medium | Medium |
| Shape in longitudinal section: ovate, medium elliptic, broad elliptic, circular, quadrangular, oblate, obovate, elongated | Circular | Broad elliptic |
| Size of pistil scar: very small, very small to small, small, small to medium, medium, medium to large, large, large to very large, very large | Medium to large | Medium |
| Rind Color (at edible maturity): | | |
| Primary color: | White RHS 155A | White RHS 157A |
| Flesh (at edible maturity): | | |
| Color Near Cavity: | Yellow green RHS 145D | Yellow green RHS 145C |
| Color in Center: | Yellow green RHS 145D | Yellow green RHS 144A |
| Color Near Rind: | Yellow green RHS 145D | Yellow green RHS 144A |
| Refractometer % Soluble Solids (Center of Flesh): | 15.37% | 10.34% |
| Penetrometer, kg: | 3.7 kg | 4.68 kg |
| Seed Cavity: | | |
| Width (mm): | 61.09 mm | 69.84 mm |
| Seeds: | | |
| Intensity of seed color: | Medium | Medium to dark |
| Disease resistances: | | |
| *Podosphaera xanthii* Race 1 | Absent | Intermediately resistant |
| *Podosphaera xanthii* Race 2 | Absent | Intermediately resistant |

TABLE 3-continued

Distinguishing Characteristics between Melon variety NUN 71560 MEM and the Reference Variety

| Characteristics | Application Variety (NUN 71560 MEM) | Reference Variety (Summer Dew) |
|---|---|---|
| *Podosphaera xanthii* Race 5 | Intermediately resistant | Absent |
| *Aphis gossypii* | Intermediately resistant | Absent |
| *Fusarium oxysporum* f. sp. *melonis* Race 0 | Susceptible | Highly resistant |

The results of the T-Test show significant differences at 5% significance level between melon variety NUN 71560 MEM and the Reference Variety for mature leaf length, mature leaf width, leaf petiole length, % soluble solids, seed cavity width, and penetrometer reading as shown in Tables 4-9.

Table 4 shows a significant difference at 5% significance level between melon variety NUN 71560 MEM and the Reference Variety (p<0.001) for mature leaf length (cm) based on the trial conducted in the US in 2022.

TABLE 4

| Statistical Parameter | Application Variety (NUN 71560 MEM) | Reference Variety (Summer Dew) |
|---|---|---|
| Number of samples | 15 | 15 |
| Minimum | 13.10 | 12.20 |
| Maximum | 18.70 | 16.40 |
| Median | 16.10 | 14.20 |
| Mean | 16.21 | 14.03 |
| Standard deviation | 1.50 | 1.05 |

Table 5 shows a significant difference at 5% significance level between melon variety NUN 71560 MEM and the Reference Variety (p=0.002) for mature leaf width (cm) based on the trial conducted in the US in 2022.

TABLE 5

| Statistical Parameter | Application Variety (NUN 71560 MEM) | Reference Variety (Summer Dew) |
|---|---|---|
| Number of samples | 15 | 15 |
| Minimum | 12.10 | 12.40 |
| Maximum | 17.90 | 16.40 |
| Median | 16.30 | 14.40 |
| Mean | 15.77 | 14.13 |
| Standard deviation | 1.42 | 1.11 |

Table 6 shows a significant difference at 5% significance level between melon variety NUN 71560 MEM and the Reference Variety (p=0.001) for leaf petiole length (cm) based on the trial conducted in the US in 2022.

TABLE 6

| Statistical Parameter | Application Variety (NUN 71560 MEM) | Reference Variety (Summer Dew) |
|---|---|---|
| Number of samples | 15 | 15 |
| Minimum | 14.10 | 11.20 |
| Maximum | 21.20 | 23.70 |
| Median | 18.70 | 14.20 |
| Mean | 18.44 | 14.73 |
| Standard deviation | 2.04 | 3.05 |

Table 7 shows a significant difference at 5% significance level between melon variety NUN 71560 MEM and the Reference Variety (p<0.001) for soluble solids (%) based on the trial conducted in the US in 2022.

TABLE 7

| Statistical Parameter | Application Variety (NUN 71560 MEM) | Reference Variety (Summer Dew) |
|---|---|---|
| Number of samples | 15 | 15 |
| Minimum | 11.30 | 7.60 |
| Maximum | 18.0 | 13.60 |
| Median | 15.30 | 10.10 |
| Mean | 15.37 | 10.34 |
| Standard deviation | 1.90 | 1.71 |

Table 8 shows a significant difference at 5% significance level between melon variety NUN 71560 MEM and the Reference Variety (p=0.001) for seed cavity width (mm) based on the trial conducted in the US in 2022.

TABLE 8

| Statistical Parameter | Application Variety (NUN 71560 MEM) | Reference Variety (Summer Dew) |
|---|---|---|
| Number of samples | 15 | 15 |
| Minimum | 51.41 | 57.38 |
| Maximum | 71.43 | 83.03 |
| Median | 61.64 | 70.44 |
| Mean | 61.09 | 69.84 |
| Standard deviation | 6.27 | 6.82 |

Table 9 shows a significant difference at 5% significance level between melon variety NUN 71560 MEM and the Reference Variety (p=0.007) for penetrometer reading (kg) based on the trial conducted in the US in 2022.

TABLE 9

| Statistical Parameter | Application Variety (NUN 71560 MEM) | Reference Variety (Summer Dew) |
|---|---|---|
| Number of samples | 15 | 15 |
| Minimum | 3.0 | 2.80 |
| Maximum | 4.50 | 7.40 |
| Median | 3.60 | 4.60 |
| Mean | 3.70 | 4.68 |
| Standard deviation | 0.48 | 1.16 |

The results of the T-Test show no significant difference at 5% significance level between melon variety NUN 71560 MEM and the Reference Variety for leaf petiole width, mature fruit weight, mature fruit length, mature fruit diameter, blossom scar diameter, peduncle length, peduncle width, thickness at medial, and seed cavity length as shown in Table 10-18.

Table 10 shows no significant difference at 5% significance level between melon variety NUN 71560 MEM and the Reference Variety (p=0.766) for leaf petiole width (mm) based on the trial conducted in the US in 2022.

TABLE 10

| Statistical Parameter | Application Variety (NUN 71560 MEM) | Reference Variety (Summer Dew) |
| --- | --- | --- |
| Number of samples | 15 | 15 |
| Minimum | 3.66 | 4.75 |
| Maximum | 7.07 | 6.88 |
| Median | 5.67 | 5.72 |
| Mean | 5.72 | 5.65 |
| Standard deviation | 0.74 | 0.58 |

Table 11 shows no significant difference at 5% significance level between melon variety NUN 71560 MEM and the Reference Variety (p=0.190) for mature fruit weight (kg) based on the trial conducted in the US in 2022.

TABLE 11

| Statistical Parameter | Application Variety (NUN 71560 MEM) | Reference Variety (Summer Dew) |
| --- | --- | --- |
| Number of samples | 15 | 15 |
| Minimum | 1.21 | 1.60 |
| Maximum | 2.11 | 2.40 |
| Median | 1.86 | 1.80 |
| Mean | 1.76 | 1.89 |
| Standard deviation | 0.26 | 0.28 |

Table 12 shows no significant difference at 5% significance level between melon variety NUN 71560 MEM and the Reference Variety (p=0.097) for mature fruit length (cm) based on the trial conducted in the US in 2022.

TABLE 12

| Statistical Parameter | Application Variety (NUN 71560 MEM) | Reference Variety (Summer Dew) |
| --- | --- | --- |
| Number of samples | 15 | 15 |
| Minimum | 13.70 | 15.30 |
| Maximum | 18.0 | 18.90 |
| Median | 16.70 | 17.10 |
| Mean | 16.47 | 17.15 |
| Standard deviation | 1.11 | 1.03 |

Table 13 shows no significant difference at 5% significance level between melon variety NUN 71560 MEM and the Reference Variety (p=0.132) for mature fruit diameter (cm) based on the trial conducted in the US in 2022.

TABLE 13

| Statistical Parameter | Application Variety (NUN 71560 MEM) | Reference Variety (Summer Dew) |
| --- | --- | --- |
| Number of samples | 15 | 15 |
| Minimum | 13.30 | 14.10 |
| Maximum | 15.70 | 16.50 |
| Median | 14.90 | 15.0 |
| Mean | 14.81 | 15.25 |
| Standard deviation | 0.74 | 0.79 |

Table 14 shows no significant difference at 5% significance level between melon variety NUN 71560 MEM and the Reference Variety (p=0.493) for blossom scar diameter (mm) based on the trial conducted in the US in 2022.

TABLE 14

| Statistical Parameter | Application Variety (NUN 71560 MEM) | Reference Variety (Summer Dew) |
| --- | --- | --- |
| Number of samples | 15 | 15 |
| Minimum | 10.87 | 8.51 |
| Maximum | 20.88 | 26.09 |
| Median | 15.54 | 14.56 |
| Mean | 15.76 | 14.85 |
| Standard deviation | 2.46 | 4.43 |

Table 15 shows no significant difference at 5% significance level between melon variety NUN 71560 MEM and the Reference Variety (p=0.569) for peduncle length (mm) based on the trial conducted in the US in 2022.

TABLE 15

| Statistical Parameter | Application Variety (NUN 71560 MEM) | Reference Variety (Summer Dew) |
| --- | --- | --- |
| Number of samples | 15 | 15 |
| Minimum | 22.11 | 22.56 |
| Maximum | 38.79 | 47.71 |
| Median | 26.72 | 26.94 |
| Mean | 28.39 | 29.73 |
| Standard deviation | 4.60 | 7.78 |

Table 16 shows no significant difference at 5% significance level between melon variety NUN 71560 MEM and the Reference Variety (p=0.303) for peduncle width (mm) based on the trial conducted in the US in 2022.

TABLE 16

| Statistical Parameter | Application Variety (NUN 71560 MEM) | Reference Variety (Summer Dew) |
| --- | --- | --- |
| Number of samples | 15 | 15 |
| Minimum | 6.42 | 5.68 |
| Maximum | 8.91 | 9.57 |
| Median | 7.36 | 7.97 |
| Mean | 7.57 | 7.93 |
| Standard deviation | 0.78 | 1.04 |

Table 17 shows no significant difference at 5% significance level between melon variety NUN 71560 MEM and the Reference Variety (p=0.448) for thickness at medial (mm) based on the trial conducted in the US in 2022.

TABLE 17

| Statistical Parameter | Application Variety (NUN 71560 MEM) | Reference Variety (Summer Dew) |
| --- | --- | --- |
| Number of samples | 15 | 15 |
| Minimum | 32.50 | 38.79 |
| Maximum | 50.53 | 52.98 |
| Median | 45.34 | 46.15 |
| Mean | 44.28 | 45.47 |
| Standard deviation | 4.66 | 3.77 |

Table 18 shows no significant difference at 5% significance level between melon variety NUN 71560 MEM and the Reference Variety (p=0.166) for seed cavity length (mm) based on the trial conducted in the US in 2022.

TABLE 18

| Statistical Parameter | Application Variety (NUN 71560 MEM) | Reference Variety (Summer Dew) |
|---|---|---|
| Number of samples | 15 | 15 |
| Minimum | 85.0 | 91.05 |
| Maximum | 116.63 | 120.61 |
| Median | 102.17 | 105.19 |
| Mean | 101.61 | 105.35 |
| Standard deviation | 7.40 | 6.98 |

The invention claimed is:

1. A plant or seed of melon variety NUN 71560 MEM, wherein a representative sample of seed of said melon variety NUN 71560 MEM has been deposited under Accession Number NCIMB 44082.

2. A plant part of the plant of claim 1, wherein said plant part is a leaf, a fruit, a scion, a root, a rootstock, or a cutting.

3. A seed that produces the plant of claim 1.

4. A melon plant or part thereof having all of the physiological and morphological characteristics of the plant of claim 1 or part thereof when grown under the same environmental conditions.

5. A tissue culture or cell culture comprising regenerable cells of the plant or plant part of claim 1, wherein said cells are obtained from melon variety NUN 71560 MEM and are suitable for regeneration into a plant having all of the physiological and morphological characteristics of melon variety NUN 71560 MEM.

6. The tissue culture or cell culture according to claim 5, comprising cells or protoplasts obtained from a plant part suitable for vegetative reproduction, wherein the plant part is a meristem, a fruit, a leaf, a petiole, a shoot, a stem, a root, a root tip, a cutting, a hypocotyl, a cotyledon, a scion, a stock, a rootstock, a pistil, an anther, a flower, a seed, a stem, or a stalk.

7. A method of producing the plant of claim 1 or a part thereof, said method comprising vegetatively propagating at least a part of the plant of melon variety NUN 71560 MEM, wherein a representative sample of seed of said melon variety NUN 71560 MEM has been deposited under Accession Number NCIMB 44082.

8. The method of claim 7, wherein said vegetatively propagating comprises regenerating a whole plant from said part of the plant of melon variety NUN 71560 MEM, wherein a representative sample of seed of said melon variety NUN 71560 MEM has been deposited under Accession Number NCIMB 44082.

9. The method of claim 7, wherein said part is a cutting, a cell culture, or a tissue culture.

10. A vegetatively propagated plant or a part thereof, produced by the method of claim 7, wherein the plant has all of the physiological and morphological characteristics of the plant of melon variety NUN 71560 MEM when grown under the same environmental conditions, and wherein a representative sample of seed of said melon variety NUN 71560 MEM has been deposited under Accession Number NCIMB 44082.

11. A method of producing a melon plant, said method comprising crossing the plant of claim 1 with a second plant at least once, selecting a progeny melon plant from said crossing and optionally allowing the progeny melon plant to form seed.

12. A method of producing a melon seed, said method comprising crossing melon plants and harvesting the resultant seed, wherein at least one melon plant is the plant of claim 1, wherein a representative sample of seed of said melon variety NUN 71560 MEM has been deposited under Accession Number NCIMB 44082.

13. A method of introducing a single locus conversion into the plant of claim 1, comprising:
a. crossing the plant of claim 1 with a second melon plant comprising a desired single locus to produce F1 progeny plants;
b. selecting F1 progeny plants that have the single locus to produce selected F1 progeny plants;
c. crossing the selected F1 progeny plants with melon variety NUN 71560 MEM to produce backcross progeny plants;
d. selecting backcross progeny plants that have the single locus and otherwise comprise all of the physiological and morphological characteristics of melon variety NUN 71560 MEM to produce selected backcross progeny plants; and
e. repeating steps (c) and (d) one or more times in succession to produce selected second or higher backcross progeny plants that comprise the single locus conversion and otherwise comprise all of the physiological and morphological characteristics of melon variety NUN 71560 MEM, wherein a representative sample of seed of said melon variety NUN 71560 MEM has been deposited under Accession Number NCIMB 44082.

14. The method of claim 13, wherein the single locus conversion confers male sterility, herbicide tolerance, insect resistance, pest resistance, disease resistance, environmental stress tolerance, modified carbohydrate metabolism, or modified metabolism.

15. A melon plant produced by the method of claim 13, wherein the plant comprises the single locus conversion and otherwise has all of the morphological and physiological characteristics of the plant of melon variety NUN 71560 MEM.

16. A method of producing doubled haploid cells of the plant of claim 1, said method comprising making double haploid cells from haploid cells from the plant or seed of melon variety NUN 71560 MEM, wherein a representative sample of seed of said melon variety NUN 71560 MEM has been deposited under Accession Number NCIMB 44082.

17. A method of grafting the scion or rootstock of the plant of claim 1, said method comprising attaching tissue from the scion or rootstock of claim 2 to the tissue of a second plant, and optionally regenerating a plant therefrom.

18. A container comprising the plant or seed of claim 1.

19. A food product, or a feed product, or a processed product comprising the plant part of claim 2, wherein the plant part comprises at least a regenerable cell of melon variety NUN 71560 MEM.

20. A method of introducing a desired trait into the plant of claim 1, said method comprises transforming the plant of claim 1 with a transgene that confers the desired trait, and wherein the desired trait is male sterility, herbicide tolerance, insect resistance, pest resistance, disease resistance, environmental stress tolerance, modified carbohydrate metabolism, or modified metabolism.

21. A melon plant produced by the method of claim 20, wherein the transformed plant contains the desired trait and otherwise has all of the morphological and physiological characteristics of melon variety NUN 71560 MEM.

22. A method of producing a modified melon plant having a desired trait, said method comprising mutating the melon plant or plant part of claim 1 and selecting the mutated plant with a desired trait, wherein the mutated plant contains the desired trait and otherwise has all of the physiological and morphological characteristics of melon variety NUN 71560 MEM when grown under the same environmental conditions, wherein a representative sample of seed of said melon variety has been deposited under Accession Number NCIMB 44082, and wherein the desired trait is male sterility, herbicide tolerance, insect resistance, pest resistance, disease resistance, environmental stress tolerance, modified carbohydrate metabolism, or modified metabolism.

23. A method of producing a melon fruit, said method comprising growing the plant of claim 1 until it sets at least one fruit and collecting at least one fruit.

24. A melon fruit produced by the method of claim 23.

25. A container comprising the fruit or part thereof produced by the method of claim 23.

26. A method for determining the genotype of the plant of claim 1, said method comprising obtaining a sample of nucleic acids from said plant, detecting in said nucleic acid a plurality of polymorphisms, thereby determining the genotype of the plant, and storing the results of detecting the plurality of polymorphisms on a computer readable medium.

27. A method for developing a melon plant in a melon breeding program, said method comprises applying plant breeding techniques to the plant of claim 1 or part thereof.

28. A method of producing a melon plant obtained from the plant of claim 1, comprising:
 a. producing a progeny melon plant derived from melon variety NUN 71560 MEM by crossing the plant of claim 1 with itself or with a second melon plant;
 b. crossing the progeny plant with itself or a different melon plant to produce seed of a progeny plant of a subsequent generation;
 c. growing a progeny plant of the subsequent generation from said seed and crossing the progeny plant of the subsequent generation with itself or another melon plant; and
 d. repeating steps (b) and (c) for at least one more generation to produce a melon plant derived from melon variety NUN 71560 MEM.

29. A method of producing a modified melon plant, said method comprising mutating a target gene by targeted gene editing in melon plant or plant part of melon variety NUN 71560 MEM, wherein the target gene modifies a desired trait, and wherein the desired trait is male sterility, herbicide tolerance, insect resistance, pest resistance, disease resistance, environmental stress tolerance, modified carbohydrate metabolism, or modified metabolism.

* * * * *